(12) United States Patent
Shiotsuka et al.

(10) Patent No.: US 7,855,180 B2
(45) Date of Patent: Dec. 21, 2010

(54) STRUCTURE AND METHOD FOR RELEASING SUBSTANCE THEREFROM

(75) Inventors: Hidenori Shiotsuka, Ebina (JP); Takeshi Imamura, Chigasaki (JP); Izumi Kumagai, Sendai (JP)

(73) Assignee: Canon Kabushiki Kaisha, Tokyo (JP)

( * ) Notice: Subject to any disclaimer, the term of this patent is extended or adjusted under 35 U.S.C. 154(b) by 119 days.

(21) Appl. No.: 12/398,970

(22) Filed: Mar. 5, 2009

(65) Prior Publication Data

US 2009/0191270 A1 Jul. 30, 2009

Related U.S. Application Data

(62) Division of application No. 11/094,132, filed on Mar. 31, 2005, now Pat. No. 7,504,086.

(30) Foreign Application Priority Data

Mar. 31, 2004 (JP) .............................. 2004-108329

(51) Int. Cl.
- A61K 38/16 (2006.01)
- A61K 31/555 (2006.01)
- A61K 31/695 (2006.01)

(52) U.S. Cl. .................. 514/21.2; 514/184; 514/65; 977/700; 977/705; 977/721; 977/722

(58) Field of Classification Search ................. None
See application file for complete search history.

(56) References Cited

U.S. PATENT DOCUMENTS

| | | | |
|---|---|---|---|
| 3,854,480 A | 12/1974 | Zaffaroni | |
| 6,428,579 B1 | 8/2002 | Valentini | |
| 7,504,086 B2 * | 3/2009 | Shiotsuka et al. | .......... 424/1.33 |
| 2006/0275811 A1 | 12/2006 | Hatakeyama et al. | |

| | | | |
|---|---|---|---|
| 2008/0108132 A1 | 5/2008 | Ban et al. | |

FOREIGN PATENT DOCUMENTS

JP 5-221852 8/1993

OTHER PUBLICATIONS

Cheng-Yu Lai, et al., "A Mesoporous Silica Nanosphere-Based Carrier System with Chemically Removable CdS Nanoparticle Caps for Stimuli-Responsive Controlled Release of Neurotransmitters and Drug Molecules", Journal American Chemical Society, vol. 125, No. 15, 2003, pp. 4451-4459.
M. Sarikaya, et al., "Molecular biomimetics: nanotechnology through biology", Nature Materials, vol. 2, Sep. 2003, pp. 577-585.
S. R. Sershen, et al., "Temperature-sensitive polymer-nanoshell composites for photothermally modulated drug delivery", Young Investigator Award World Biomaterials Congress 2000, May 2000, John Wiley & Sons, Inc., pp. 293-298.
M. Yokoyama, et al., "A novel drug carrier system with polymeric micelles", Drug Delivery System, vol. 6, No. 2, Mar. 1991, pp. 77-81.
H. Tsutsumi, et al., "A potentially biodegradable polyamide containing disulfide bonds as a positive material for secondary batteries", Electrochimica Acta, vol. 43, Nos. 3-4, 1998, pp. 427-429.
U.S. Appl. No. 10/548,442, International Filing Date Aug. 18, 2004, H. Shiotsuka, et al.

\* cited by examiner

*Primary Examiner*—Andrew D Kosar
*Assistant Examiner*—Satyanarayana R Gudibande
(74) *Attorney, Agent, or Firm*—Fitzpatrick, Cella, Harper & Scinto

(57) ABSTRACT

A structure comprises at least a porous body holding a substance releasably, comprising a capping member for keeping the substance inside the pore and/or on at least a part of the entire surface of the porous body, and a connecting member for connecting the porous body and the capping member separably, the connecting member comprising a biopolymer compound.

A method for releasing a substance from the structure set forth comprises the steps of applying stimulation from outside to the structure, and cleaving at least one of the bonding between the connecting member and the capping member and the bonding between the connecting member and the porous member to make the substance releasable from the structure.

1 Claim, 9 Drawing Sheets

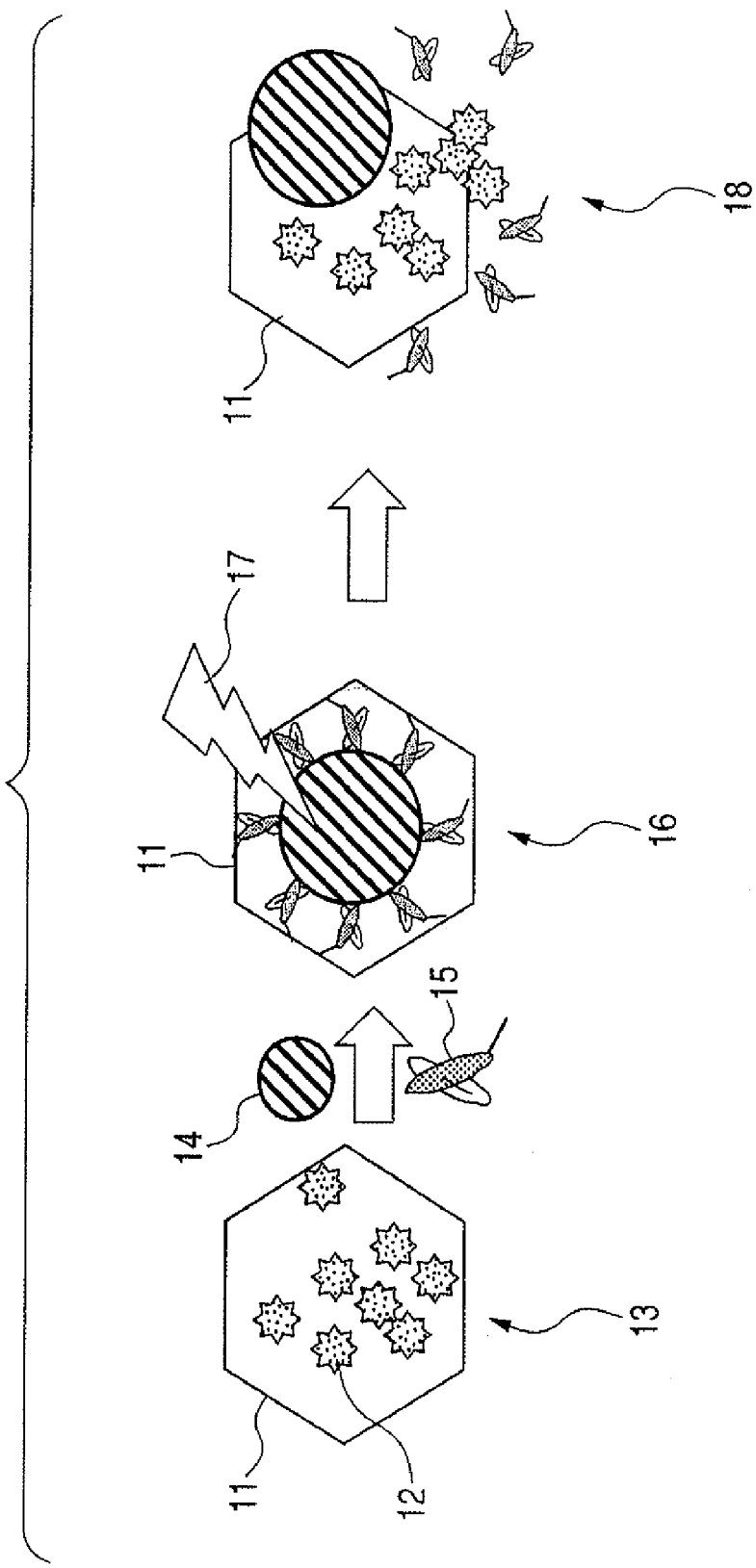

SEQUENCE LISTING

<160> NUMBER OF SEQ ID NOS: 94

<210> SEQ ID NO 1
<211> LENGTH: 5
<212> TYPE: PRT
<213> ORGANISM: Homo sapiens

<400> SEQUENCE: 1

Asp Tyr Tyr Met Asp
1          5

<210> SEQ ID NO 2
<211> LENGTH: 17
<212> TYPE: PRT
<213> ORGANISM: Homo sapiens

<400> SEQUENCE: 2

Ser Ile Lys Gln Asp Gly Ser Glu Thr Arg Tyr Gly Asp Ser Val Arg
1               5                   10                  15

Gly

<210> SEQ ID NO 3
<211> LENGTH: 9
<212> TYPE: PRT
<213> ORGANISM: Homo sapiens

<400> SEQUENCE: 3

Glu Leu Asp Gly Gly Phe Phe Asp Phe
1               5

<210> SEQ ID NO 4
<211> LENGTH: 5
<212> TYPE: PRT
<213> ORGANISM: Homo sapiens

<400> SEQUENCE: 4

Gly His Trp Met His
1               5

<210> SEQ ID NO 5
<211> LENGTH: 17
<212> TYPE: PRT
<213> ORGANISM: Homo sapiens

<400> SEQUENCE: 5

Arg Ile Asp Glu His Gly Ser Ser Ala Tyr Tyr Ala Asp Ser Val Asn
1               5                   10                  15

Gly

<210> SEQ ID NO 6
<211> LENGTH: 15
<212> TYPE: PRT
<213> ORGANISM: Homo sapiens

<400> SEQUENCE: 6

Leu Gly Phe Ile Thr Pro Glu Val Val His Trp Ser Ser Asp Ile
1               5                   10                  15

<210> SEQ ID NO 7
<211> LENGTH: 5
<212> TYPE: PRT
<213> ORGANISM: Homo sapiens

<400> SEQUENCE: 7

Arg Phe Tyr Trp Asn
1               5

<210> SEQ ID NO 8
<211> LENGTH: 16
<212> TYPE: PRT
<213> ORGANISM: Homo sapiens

<400> SEQUENCE: 8

Arg Ile Phe Thr Asn Gly Thr Thr Asn Tyr Asn Pro Ser Leu Gly Ser
1               5                   10                  15

<210> SEQ ID NO 9
<211> LENGTH: 13
<212> TYPE: PRT
<213> ORGANISM: Homo sapiens

<400> SEQUENCE: 9

Gly Gly Asp Tyr Gly Pro Ala Leu Ala Trp Phe Asp Pro
1               5                   10

<210> SEQ ID NO 10
<211> LENGTH: 10
<212> TYPE: PRT
<213> ORGANISM: Homo sapiens

<400> SEQUENCE: 10

Glu Ser Met Val Arg Asp Gly Met Asp Val
1               5                   10

<210> SEQ ID NO 11
<211> LENGTH: 5
<212> TYPE: PRT
<213> ORGANISM: Homo sapiens

<400> SEQUENCE: 11

Gly Tyr Tyr Trp Thr
1               5

<210> SEQ ID NO 12
<211> LENGTH: 16
<212> TYPE: PRT
<213> ORGANISM: Homo sapiens

<400> SEQUENCE: 12

Asp Ser Ser His Ser Gly Arg Thr Asn Tyr Asn Pro Ser Leu Lys Ser
1               5                   10                  15

<210> SEQ ID NO 13
<211> LENGTH: 9
<212> TYPE: PRT
<213> ORGANISM: Homo sapiens

<400> SEQUENCE: 13

Ala Glu Glu Thr Val Thr Ile Val Pro
1               5

<210> SEQ ID NO 14
<211> LENGTH: 5
<212> TYPE: PRT
<213> ORGANISM: Homo sapiens

<400> SEQUENCE: 14

Ser His Tyr Ile His
1               5

<210> SEQ ID NO 15
<211> LENGTH: 17
<212> TYPE: PRT
<213> ORGANISM: Homo sapiens

<400> SEQUENCE: 15

Gly Phe Ile Pro Ile Phe Gly Thr Ser Asn Tyr Ala Glu Lys Phe Lys
1               5                   10                  15

Gly

<210> SEQ ID NO 16
<211> LENGTH: 15
<212> TYPE: PRT
<213> ORGANISM: Homo sapiens

<400> SEQUENCE: 16

Pro Arg Arg Ser Ser Ser Ser Lys Thr Phe Ser Ala Leu Asp Tyr
1               5                   10                  15

<210> SEQ ID NO 17
<211> LENGTH: 5
<212> TYPE: PRT
<213> ORGANISM: Homo sapiens

<400> SEQUENCE: 17

Asp Tyr Ala Met Asn
1               5

<210> SEQ ID NO 18
<211> LENGTH: 15
<212> TYPE: PRT
<213> ORGANISM: Homo sapiens

<400> SEQUENCE: 18

Phe Ile Arg Ser Arg Gly Phe Gly Gly Thr Pro Glu Tyr Ala Ala
1               5                   10                  15

<210> SEQ ID NO 19
<211> LENGTH: 18
<212> TYPE: PRT
<213> ORGANISM: Homo sapiens

<400> SEQUENCE: 19

Asp Tyr Arg Pro Leu Gln Phe Trp Pro Gly Arg Gln Met Asp Ala Phe
1               5                   10                  15

Asp Ile

<210> SEQ ID NO 20
<211> LENGTH: 5
<212> TYPE: PRT
<213> ORGANISM: Homo sapiens

<400> SEQUENCE: 20

Ser Tyr Trp Ile Asn
1               5

<210> SEQ ID NO 21
<211> LENGTH: 17
<212> TYPE: PRT
<213> ORGANISM: Homo sapiens

<400> SEQUENCE: 21

Met Ile Tyr Pro Ala Asp Ser Asp Thr Arg Tyr Ser Pro Ser Phe Gln
1               5                   10                  15

Gly

<210> SEQ ID NO 22
<211> LENGTH: 10
<212> TYPE: PRT
<213> ORGANISM: Homo sapiens

```
<400> SEQUENCE: 22

Leu Gly Ile Gly Gly Arg Tyr Met Ser Arg
1               5                   10

<210> SEQ ID NO 23
<211> LENGTH: 5
<212> TYPE: PRT
<213> ORGANISM: Homo sapiens

<400> SEQUENCE: 23

Arg Tyr Tyr Ile His
1               5

<210> SEQ ID NO 24
<211> LENGTH: 17
<212> TYPE: PRT
<213> ORGANISM: Homo sapiens

<400> SEQUENCE: 24

Met Ile Asn Pro Arg Gly Gly Ser Thr Thr Tyr Ala Gln Lys Phe Gln
1               5                   10                  15

Gly

<210> SEQ ID NO 25
<211> LENGTH: 14
<212> TYPE: PRT
<213> ORGANISM: Homo sapiens

<400> SEQUENCE: 25

Glu Ser Met Pro Gly Arg Asp Val Arg Asp Gly Met Asp Val
1               5                   10

<210> SEQ ID NO 26
<211> LENGTH: 5
<212> TYPE: PRT
<213> ORGANISM: Homo sapiens

<400> SEQUENCE: 26

Asp His Tyr Ile His
1               5

<210> SEQ ID NO 27
<211> LENGTH: 14
<212> TYPE: PRT
<213> ORGANISM: Homo sapiens

<400> SEQUENCE: 27

Pro Asn Ser Gly Ala Thr Lys Tyr Ala Gln Lys Phe His Gly
1               5                   10

<210> SEQ ID NO 28
<211> LENGTH: 9
<212> TYPE: PRT
<213> ORGANISM: Homo sapiens

<400> SEQUENCE: 28

Gly Ile Leu Leu Ala Arg Leu Asp Val
1               5

<210> SEQ ID NO 29
<211> LENGTH: 5
<212> TYPE: PRT
<213> ORGANISM: Homo sapiens
```

<400> SEQUENCE: 29

Asn Tyr Ala Ile Ser
1               5

<210> SEQ ID NO 30
<211> LENGTH: 17
<212> TYPE: PRT
<213> ORGANISM: Homo sapiens

<400> SEQUENCE: 30

Gly Thr Leu Leu Met Leu Arg Ile Ile Asn Ser Ala Gln Lys Phe Gln
1               5                   10                  15

Gly

<210> SEQ ID NO 31
<211> LENGTH: 14
<212> TYPE: PRT
<213> ORGANISM: Homo sapiens

<400> SEQUENCE: 31

Ala Leu Pro Thr Ser Leu Gly Pro Ile Gly Tyr Leu His His
1               5                   10

<210> SEQ ID NO 32
<211> LENGTH: 5
<212> TYPE: PRT
<213> ORGANISM: Homo sapiens

<400> SEQUENCE: 32

Asp Tyr Tyr Met His
1               5

<210> SEQ ID NO 33
<211> LENGTH: 17
<212> TYPE: PRT
<213> ORGANISM: Homo sapiens

<400> SEQUENCE: 33

Trp Ile Asn Pro Asn Ile Gly Ala Thr Asn His Ala Gln Arg Phe Gln
1               5                   10                  15

Gly

<210> SEQ ID NO 34
<211> LENGTH: 9
<212> TYPE: PRT
<213> ORGANISM: Homo sapiens

<400> SEQUENCE: 34

Asp Leu Gly Ile Ser Ala Phe Glu Asn
1               5

<210> SEQ ID NO 35
<211> LENGTH: 5
<212> TYPE: PRT
<213> ORGANISM: Homo sapiens

<400> SEQUENCE: 35

Asp Tyr Phe Met His
1               5

<210> SEQ ID NO 36
<211> LENGTH: 17
<212> TYPE: PRT

<213> ORGANISM: Homo sapiens

<400> SEQUENCE: 36

Trp Ile Asn Pro Asn Ser Gly Val Thr His Tyr Ala Gln Lys Phe Gln
1               5                   10                  15
Gly

<210> SEQ ID NO 37
<211> LENGTH: 12
<212> TYPE: PRT
<213> ORGANISM: Homo sapiens

<400> SEQUENCE: 37

Glu Leu Ile Thr Gly Arg Leu Pro Thr Asp Asn Asp
1               5                   10

<210> SEQ ID NO 38
<211> LENGTH: 5
<212> TYPE: PRT
<213> ORGANISM: Homo sapiens

<400> SEQUENCE: 38

Gly Tyr Tyr Ile His
1               5

<210> SEQ ID NO 39
<211> LENGTH: 17
<212> TYPE: PRT
<213> ORGANISM: Homo sapiens

<400> SEQUENCE: 39

Trp Ile Asn Pro Asn Thr Gly Gly Thr Asn Tyr Ala Gln Lys Phe Gln
1               5                   10                  15
Gly

<210> SEQ ID NO 40
<211> LENGTH: 18
<212> TYPE: PRT
<213> ORGANISM: Homo sapiens

<400> SEQUENCE: 40

Arg Ser Gly Gly Ser Gly Arg Tyr Trp Gly Ile Lys Asn Asn Trp Phe
1               5                   10                  15
Asp Pro

<210> SEQ ID NO 41
<211> LENGTH: 17
<212> TYPE: PRT
<213> ORGANISM: Homo sapiens

<400> SEQUENCE: 41

Trp Ile Asn Pro Asn Ser Gly Val Thr His Tyr Ala Gln Lys Phe Gln
1               5                   10                  15
Gly

<210> SEQ ID NO 42
<211> LENGTH: 12
<212> TYPE: PRT
<213> ORGANISM: Homo sapiens

<400> SEQUENCE: 42

Glu Leu Ile Ala Gly Arg Leu Pro Thr Asp Asn Asp

```
<210> SEQ ID NO 43
<211> LENGTH: 5
<212> TYPE: PRT
<213> ORGANISM: Homo sapiens

<400> SEQUENCE: 43

Asp Tyr Tyr Phe His
1               5

<210> SEQ ID NO 44
<211> LENGTH: 17
<212> TYPE: PRT
<213> ORGANISM: Homo sapiens

<400> SEQUENCE: 44

Trp Ile Asn Phe Asp Ser Gly Gly Thr Asn Tyr Ala Gln Lys Phe Gln
1               5                   10                  15

Gly

<210> SEQ ID NO 45
<211> LENGTH: 13
<212> TYPE: PRT
<213> ORGANISM: Homo sapiens

<400> SEQUENCE: 45

Gly Ser Arg Tyr Asn Ser Gly Trp Tyr Tyr Phe Asp Tyr
1               5                   10

<210> SEQ ID NO 46
<211> LENGTH: 5
<212> TYPE: PRT
<213> ORGANISM: Homo sapiens

<400> SEQUENCE: 46

Ile Ser Ser Pro Thr
1               5

<210> SEQ ID NO 47
<211> LENGTH: 16
<212> TYPE: PRT
<213> ORGANISM: Homo sapiens

<400> SEQUENCE: 47

Glu Ile Tyr His Ser Gly Thr Ser His His Asn Pro Ser Leu Lys Asn
1               5                   10                  15

<210> SEQ ID NO 48
<211> LENGTH: 11
<212> TYPE: PRT
<213> ORGANISM: Homo sapiens

<400> SEQUENCE: 48

Leu Asp Phe Asp Ser Pro Leu Gly Met Asp Ala
1               5                   10

<210> SEQ ID NO 49
<211> LENGTH: 11
<212> TYPE: PRT
<213> ORGANISM: Homo sapiens

<400> SEQUENCE: 49

Arg Ala Ser Gln Ser Ile Ser Thr Tyr Leu Asn
```

```
1               5                   10
```

<210> SEQ ID NO 50
<211> LENGTH: 7
<212> TYPE: PRT
<213> ORGANISM: Homo sapiens

<400> SEQUENCE: 50

```
Ala Ala Ser Ser Leu Gln Ser
1               5
```

<210> SEQ ID NO 51
<211> LENGTH: 9
<212> TYPE: PRT
<213> ORGANISM: Homo sapiens

<400> SEQUENCE: 51

```
Gln Gln Ser Tyr Ser Thr Pro Arg Thr
1               5
```

<210> SEQ ID NO 52
<211> LENGTH: 11
<212> TYPE: PRT
<213> ORGANISM: Homo sapiens

<400> SEQUENCE: 52

```
Arg Ala Ser Glu Asp Val Asn Ser Trp Leu Ala
1               5                   10
```

<210> SEQ ID NO 53
<211> LENGTH: 7
<212> TYPE: PRT
<213> ORGANISM: Homo sapiens

<400> SEQUENCE: 53

```
Gly Ser Thr Asn Leu Gln Gly
1               5
```

<210> SEQ ID NO 54
<211> LENGTH: 10
<212> TYPE: PRT
<213> ORGANISM: Homo sapiens

<400> SEQUENCE: 54

```
Lys Tyr Phe Asp Ala Leu Pro Pro Val Thr
1               5                   10
```

<210> SEQ ID NO 55
<211> LENGTH: 17
<212> TYPE: PRT
<213> ORGANISM: Homo sapiens

<400> SEQUENCE: 55

```
Thr Ser Ser Gln Ser Leu Leu Tyr Thr Ser Asn Asn Lys Asn Tyr Leu
1               5                   10                  15

Thr
```

<210> SEQ ID NO 56
<211> LENGTH: 7
<212> TYPE: PRT
<213> ORGANISM: Homo sapiens

<400> SEQUENCE: 56

```
Trp Ala Ser Thr Arg Glu Phe
```

<210> SEQ ID NO 57
<211> LENGTH: 9
<212> TYPE: PRT
<213> ORGANISM: Homo sapiens

<400> SEQUENCE: 57

Gln Gln Tyr Ser Asp Pro Pro Thr
1               5

<210> SEQ ID NO 58
<211> LENGTH: 124
<212> TYPE: PRT
<213> ORGANISM: Homo sapiens

<400> SEQUENCE: 58

Glu Val Gln Val Val Glu Ser Gly Ala Glu Val Lys Lys Pro Gly Ala
1               5                   10                  15

Ser Val Lys Val Ser Cys Lys Ala Ser Gly Tyr Thr Phe Asn Ser His
            20                  25                  30

Tyr Ile His Trp Val Arg Gln Ala Pro Gly Gln Gly Leu Glu Trp Met
        35                  40                  45

Gly Gly Phe Ile Pro Ile Phe Gly Thr Ser Asn Tyr Ala Glu Lys Phe
    50                  55                  60

Lys Gly Arg Val Thr Phe Thr Val Asp Thr Ser Thr Asn Thr Ala His
65                  70                  75                  80

Met Glu Leu Thr Arg Leu Arg Ser Glu Asp Thr Ala Ile Tyr Tyr Cys
                85                  90                  95

Ala Leu Pro Arg Arg Ser Ser Ser Lys Thr Phe Ser Ala Leu Asp
            100                 105                 110

Tyr Trp Gly Gln Gly Thr Leu Val Thr Val Ser Ser
        115                 120

<210> SEQ ID NO 59
<211> LENGTH: 129
<212> TYPE: PRT
<213> ORGANISM: Homo sapiens

<400> SEQUENCE: 59

Gln Val Gln Leu Thr Glu Ser Gly Gly Gly Leu Val Gln Pro Gly Arg
1               5                   10                  15

Ser Leu Arg Leu Ser Cys Thr Ala Ser Gly Phe Thr Leu Gly Asp Tyr
            20                  25                  30

Ala Met Asn Trp Val Arg Gln Ala Pro Gly Lys Gly Leu Glu Trp Val
        35                  40                  45

Gly Phe Ile Arg Ser Arg Gly Phe Gly Gly Thr Pro Glu Tyr Ala Ala
    50                  55                  60

Ser Val Lys Gly Arg Phe Thr Ile Ser Arg Asp Asn Ser Lys Gly Ile
65                  70                  75                  80

Ala Tyr Leu Glu Met Asn Ser Leu Lys Thr Glu Asp Thr Ala Met Tyr
                85                  90                  95

Tyr Cys Thr Arg Asp Tyr Arg Pro Leu Gln Phe Trp Pro Gly Arg Gln
            100                 105                 110

Met Asp Ala Phe Asp Ile Trp Gly Gln Gly Thr Met Val Thr Val Ser
        115                 120                 125

Ser

<210> SEQ ID NO 60
<211> LENGTH: 120
<212> TYPE: PRT
<213> ORGANISM: Homo sapiens

<400> SEQUENCE: 60

Gln Val Gln Leu Val Glu Ser Gly Ala Glu Val Lys Lys Ala Gly Glu
1               5                   10                  15

Ser Leu Lys Ile Ser Cys Lys Gly Ser Gly Tyr Ser Phe Pro Ser Tyr
            20                  25                  30

Trp Ile Asn Trp Val Arg Gln Met Pro Gly Lys Gly Leu Glu Trp Met
        35                  40                  45

Gly Met Ile Tyr Pro Ala Asp Ser Asp Thr Arg Tyr Ser Pro Ser Phe
    50                  55                  60

Gln Gly His Val Thr Ile Ser Ala Asp Lys Ser Ile Asn Thr Ala Tyr
65                  70                  75                  80

Leu Gln Trp Ala Gly Leu Lys Ala Ser Asp Thr Ala Ile Tyr Tyr Cys
                85                  90                  95

Ala Arg Leu Gly Ile Gly Gly Arg Tyr Met Ser Arg Trp Gly Gln Gly
            100                 105                 110

Thr Leu Val Thr Val Ser Ser Ala
        115                 120

<210> SEQ ID NO 61
<211> LENGTH: 119
<212> TYPE: PRT
<213> ORGANISM: Homo sapiens

<400> SEQUENCE: 61

Gln Val Gln Leu Val Gln Ser Gly Ala Glu Val Lys Lys Pro Gly Ala
1               5                   10                  15

Ser Val Lys Val Ser Cys Glu Ala Ser Gly Tyr Thr Phe Thr Arg Tyr
            20                  25                  30

Tyr Ile His Trp Val Arg Gln Ala Pro Gly Gln Gly Leu Glu Trp Met
        35                  40                  45

Gly Met Ile Asn Pro Arg Gly Gly Ser Thr Thr Tyr Ala Gln Lys Phe
    50                  55                  60

Gln Gly Arg Val Thr Met Thr Arg Asp Arg Ser Thr Ser Thr Val His
65                  70                  75                  80

Met Glu Val Ser Ser Leu Arg Ser Asp Asp Thr Ala Val Tyr Tyr Cys
                85                  90                  95

Ala Arg Glu Ser Met Val Arg Asp Gly Met Asp Val Trp Gly Gln Gly
            100                 105                 110

Thr Thr Val Thr Val Ser Ser
        115

<210> SEQ ID NO 62
<211> LENGTH: 118
<212> TYPE: PRT
<213> ORGANISM: Homo sapiens

<400> SEQUENCE: 62

Glu Val Gln Leu Val Glu Ser Gly Ser Glu Val Lys Lys Pro Gly Ala
1               5                   10                  15

Ser Leu Lys Val Ser Cys Lys Ala Ser Gly Tyr Ser Phe Val Asp His
            20                  25                  30

Tyr Ile His Trp Val Arg Gln Ala Pro Gly Gln Gly Leu Glu Trp Met

-continued

```
                35                  40                  45
Gly Trp Leu Asn Pro Asn Ser Gly Ala Thr Lys Tyr Ala Gln Lys Phe
 50                  55                  60
His Gly Arg Val Thr Leu Thr Arg Asp Thr Ser Ile Ser Thr Val Tyr
 65                  70                  75                  80
Met Glu Leu Ser Arg Leu Ile Ser Asp Asp Thr Ala Val Tyr Phe Cys
                 85                  90                  95
Ala Arg Gly Ile Leu Leu Ala Arg Leu Asp Val Trp Gly Gln Gly Thr
                100                 105                 110
Leu Val Thr Val Ser Ser
        115

<210> SEQ ID NO 63
<211> LENGTH: 118
<212> TYPE: PRT
<213> ORGANISM: Homo sapiens

<400> SEQUENCE: 63

Gln Val Gln Leu Val Gln Ser Gly Gly Gly Leu Val Gln Pro Gly Gly
 1               5                  10                  15
Ser Leu Arg Leu Ser Cys Ala Ala Ser Gly Phe Thr Phe Ser Asp Tyr
                20                  25                  30
Tyr Met Asp Trp Val Arg Gln Ala Pro Gly Lys Gly Leu Gln Trp Val
                35                  40                  45
Ala Ser Ile Lys Gln Asp Gly Ser Glu Thr Arg Tyr Gly Asp Ser Val
 50                  55                  60
Arg Gly Arg Phe Ile Ile Ser Arg Asp Asn Thr Lys Asn Ser Ala Tyr
 65                  70                  75                  80
Leu Gln Met Asn Thr Leu Ser Ala Glu Asp Arg Ala Val Tyr His Cys
                 85                  90                  95
Val Arg Glu Leu Asp Gly Gly Phe Phe Asp Phe Trp Gly Gln Gly Thr
                100                 105                 110
Leu Val Thr Val Ser Ser
        115

<210> SEQ ID NO 64
<211> LENGTH: 121
<212> TYPE: PRT
<213> ORGANISM: Homo sapiens

<400> SEQUENCE: 64

Gln Val Gln Leu Gln Glu Ser Gly Pro Gly Leu Val Lys Pro Ser Glu
 1               5                  10                  15
Thr Leu Ser Leu Thr Cys Ser Val Ser Gly Ala Ser Met Ser Arg Phe
                20                  25                  30
Tyr Trp Asn Trp Ile Arg His Ser Ala Gly Lys Gly Leu Glu Trp Ile
                35                  40                  45
Gly Arg Ile Phe Thr Asn Gly Thr Thr Asn Tyr Asn Pro Ser Leu Gly
 50                  55                  60
Ser Arg Val Thr Met Ser Val Asp Thr Ala Lys Asn Gln Phe Ser Leu
 65                  70                  75                  80
Arg Val Thr Ser Val Thr Ala Ala Asp Ala Val Tyr Tyr Cys Ala
                 85                  90                  95
Arg Gly Gly Asp Tyr Gly Pro Ala Leu Ala Trp Phe Asp Pro Trp Gly
                100                 105                 110
Gln Gly Thr Leu Val Thr Val Ser Ser
```

-continued

<210> SEQ ID NO 65
<211> LENGTH: 124
<212> TYPE: PRT
<213> ORGANISM: Homo sapiens

<400> SEQUENCE: 65

Gln Val Gln Leu Gln Glu Trp Gly Gly Val Val Gln Pro Gly Arg
1               5                   10                  15

Ser Leu Arg Leu Ser Cys Val Ala Ser Gly Phe Thr Phe Ser Gly His
                20                  25                  30

Trp Met His Trp Val Arg Gln Ala Pro Gly Lys Gly Leu Val Trp Val
            35                  40                  45

Ser Arg Ile Asp Glu His Gly Ser Ser Ala Tyr Tyr Ala Asp Ser Val
    50                  55                  60

Asn Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Phe Ile Thr Pro Glu Val Val His Ser Ser Asp
            100                 105                 110

Ile Trp Gly Gln Gly Thr Met Val Thr Val Ser Ser
        115                 120

<210> SEQ ID NO 66
<211> LENGTH: 119
<212> TYPE: PRT
<213> ORGANISM: Homo sapiens

<400> SEQUENCE: 66

Gln Val Gln Leu Val Gln Ser Gly Ala Glu Val Lys Lys Pro Gly Ala
1               5                   10                  15

Ser Val Lys Val Ser Cys Glu Ala Ser Gly Tyr Thr Phe Thr Arg Tyr
                20                  25                  30

Tyr Ile His Trp Val Arg Gln Ala Pro Gly Gln Gly Leu Glu Trp Met
            35                  40                  45

Gly Met Ile Asn Pro Arg Gly Gly Ser Thr Thr Tyr Ala Gln Lys Phe
    50                  55                  60

Gln Gly Arg Val Thr Met Thr Arg Asp Arg Ser Thr Ser Thr Val His
65                  70                  75                  80

Met Glu Val Ser Ser Leu Arg Ser Asp Asp Thr Ala Val Tyr Tyr Cys
                85                  90                  95

Ala Arg Glu Ser Met Val Arg Asp Gly Met Asp Val Trp Gly Gln Gly
            100                 105                 110

Thr Thr Val Thr Val Ser Ser
        115

<210> SEQ ID NO 67
<211> LENGTH: 128
<212> TYPE: PRT
<213> ORGANISM: Homo sapiens

<400> SEQUENCE: 67

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
                20                  25                  30

Tyr Trp Thr Trp Ile Arg Gln Pro Pro Gly Lys Gly Leu Glu Trp Ile
            35                  40                  45

Gly Asp Ser Ser His Ser Gly Arg Thr Asn Tyr Asn Pro Ser Leu Lys
 50                  55                  60

Ser Arg Val Thr Ile Ser Val Asp Ala Ser Lys Lys Gln Phe Ser Leu
 65                  70                  75                  80

Lys Leu Ile Ser Val Thr Ala Ala Glu Pro Phe Arg Ser Ser Ser Glu
                 85                  90                  95

Met Ser Phe Cys Ser Leu Ala Glu Glu Thr Val Thr Ile Val Pro Trp
            100                 105                 110

Pro Gln Thr Ser Lys Ala Pro Pro Asn Arg Pro Arg Cys Phe Val Ser
            115                 120                 125

<210> SEQ ID NO 68
<211> LENGTH: 125
<212> TYPE: PRT
<213> ORGANISM: Homo sapiens

<400> SEQUENCE: 68

Gly Ala Ala Gly Glu Ser Gly Ala Glu Val Arg Lys Pro Gly Ser Ser
 1               5                  10                  15

Val Lys Val Ser Cys Lys Ala Ser Gly Gly Ser Ile Asn Asn Tyr Ala
                 20                  25                  30

Ile Ser Trp Val Arg Gln Ala Pro Gly Gln Gly Leu Glu Trp Ile Gly
            35                  40                  45

Gly Thr Leu Leu Met Leu Arg Ile Ile Asn Ser Ala Gln Lys Phe Gln
 50                  55                  60

Gly Arg Val Ser Ile Thr Ala Asp Thr Ser Thr Asn Thr Ala Tyr Met
 65                  70                  75                  80

Glu Leu Ser Ser Leu Arg Ser Glu Asp Thr Ala Met Tyr Tyr Cys Ala
                 85                  90                  95

Ser Ser Val Ala Ala Leu Pro Thr Ser Leu Gly Pro Ile Gly Tyr Leu
            100                 105                 110

His His Trp Gly Gln Gly Thr Leu Val Thr Val Ser Ser
            115                 120                 125

<210> SEQ ID NO 69
<211> LENGTH: 117
<212> TYPE: PRT
<213> ORGANISM: Homo sapiens

<400> SEQUENCE: 69

Gly Ala Gly Gly Glu Ser Gly Ala Asp Val Lys Lys Pro Gly Ala Ser
 1               5                  10                  15

Val Lys Val Ser Cys Lys Ala Ser Gly Tyr Thr Phe Thr Asp Tyr Tyr
                 20                  25                  30

Met His Trp Val Arg Gln Ala Pro Gly Gln Gly Leu Glu Trp Met Gly
            35                  40                  45

Trp Ile Asn Pro Asn Ile Gly Ala Thr Asn His Ala Gln Arg Phe Gln
 50                  55                  60

Gly Arg Leu Thr Val Ser Arg Asp Thr Ser Ile Thr Thr Val Tyr Met
 65                  70                  75                  80

Glu Leu Ser Arg Leu Gln Ser Asp Asp Thr Ala Val Tyr Phe Cys Ala
                 85                  90                  95

Arg Asp Leu Gly Ile Ser Ala Phe Glu Asn Trp Gly Gln Gly Thr Met
            100                 105                 110

```
Val Thr Val Ser Ser
        115

<210> SEQ ID NO 70
<211> LENGTH: 120
<212> TYPE: PRT
<213> ORGANISM: Homo sapiens

<400> SEQUENCE: 70

Gly Asp Gly Gly Glu Ser Gly Ala Glu Val Arg Lys Pro Gly Ala Ser
1               5                   10                  15

Val Lys Val Ser Cys Lys Ala Ser Arg Tyr Ser Phe Thr Asp Tyr Phe
            20                  25                  30

Met His Trp Val Arg Gln Ala Pro Gly Gln Gly Leu Glu Trp Met Gly
        35                  40                  45

Trp Ile Asn Pro Asn Ser Gly Val Thr His Tyr Ala Gln Lys Phe Gln
    50                  55                  60

Gly Arg Val Thr Met Thr Arg Asp Thr Ser Ile Asn Thr Ala Tyr Met
65                  70                  75                  80

Glu Val Ser Arg Leu Arg Tyr Asp Asp Thr Ala Val Tyr Tyr Cys Thr
                85                  90                  95

Arg Glu Leu Ile Thr Gly Arg Leu Pro Thr Asp Asn Asp Trp Gly Gln
            100                 105                 110

Gly Thr Leu Val Thr Val Ser Ser
        115                 120

<210> SEQ ID NO 71
<211> LENGTH: 126
<212> TYPE: PRT
<213> ORGANISM: Homo sapiens

<400> SEQUENCE: 71

Gly Ala Ala Gly Glu Ser Gly Ala Glu Val Arg Lys Pro Gly Ala Ser
1               5                   10                  15

Val Lys Val Ser Cys Lys Thr Ser Gly Tyr Asn Phe Arg Gly Tyr Tyr
            20                  25                  30

Ile His Trp Val Arg Gln Ala Pro Gly Gln Gly Leu Glu Trp Met Gly
        35                  40                  45

Trp Ile Asn Pro Asn Thr Gly Thr Asn Tyr Ala Gln Lys Phe Gln
    50                  55                  60

Gly Arg Val Thr Met Thr Arg Asp Thr Ser Ile Asn Thr Ala Tyr Met
65                  70                  75                  80

Glu Val Ser Lys Leu Arg Ser Asp Asp Thr Ala Val Tyr Tyr Cys Ala
                85                  90                  95

Arg Arg Ser Gly Gly Ser Gly Arg Tyr Trp Gly Ile Lys Asn Asn Trp
            100                 105                 110

Phe Asp Pro Trp Gly Gln Gly Thr Leu Val Thr Val Ser Ser
        115                 120                 125

<210> SEQ ID NO 72
<211> LENGTH: 120
<212> TYPE: PRT
<213> ORGANISM: Homo sapiens

<400> SEQUENCE: 72

Gly Asp Gly Gly Glu Ser Gly Ala Glu Val Arg Lys Pro Gly Ala Ser
1               5                   10                  15
```

Val Lys Val Ser Cys Lys Ala Ser Arg Tyr Ser Phe Thr Asp Tyr Phe
            20                  25                  30

Met His Trp Val Arg Gln Ala Pro Gly Gln Gly Leu Glu Trp Met Gly
        35                  40                  45

Trp Ile Asn Pro Asn Ser Gly Val Thr His Tyr Ala Gln Lys Phe Gln
    50                  55                  60

Gly Arg Val Thr Met Thr Arg Asp Thr Ser Ile Asn Thr Ala Tyr Met
65                  70                  75                  80

Glu Val Ser Arg Leu Arg Tyr Asp Asp Thr Ala Val Tyr Tyr Cys Thr
                85                  90                  95

Arg Glu Leu Ile Ala Gly Arg Leu Pro Thr Asp Asn Asp Trp Gly Gln
            100                 105                 110

Gly Thr Leu Val Thr Val Ser Ser
        115                 120

<210> SEQ ID NO 73
<211> LENGTH: 122
<212> TYPE: PRT
<213> ORGANISM: Homo sapiens

<400> SEQUENCE: 73

Gln Val Gln Leu Val Gln Ser Gly Ala Glu Val Lys Lys Pro Gly Ala
1               5                   10                  15

Ser Val Lys Val Ser Cys Lys Ala Ala Gly Tyr Thr Phe Thr Asp Tyr
            20                  25                  30

Tyr Phe His Trp Val Arg Gln Ala Pro Gly Gln Gly Leu Glu Trp Met
        35                  40                  45

Gly Trp Ile Asn Pro Asp Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Asp Leu Ser Arg Leu Arg Ser Asp Asp Thr Ala Val Cys Tyr Cys
                85                  90                  95

Ala Arg Gly Ser Arg Tyr Asn Ser Gly Trp Tyr Tyr Phe Asp Tyr Trp
            100                 105                 110

Ser Arg Gly Thr Leu Val Thr Val Ser Ser
        115                 120

<210> SEQ ID NO 74
<211> LENGTH: 120
<212> TYPE: PRT
<213> ORGANISM: Homo sapiens

<400> SEQUENCE: 74

Gln Val Gln Leu Gln Glu Trp Gly Pro Gly Leu Val Lys Pro Ser Gly
1               5                   10                  15

Thr Leu Ser Leu Thr Cys Ala Val Ser Gly Gly Thr Ile Ser Ser Pro
            20                  25                  30

Thr Trp Trp Asn Trp Val Arg Gln Pro Pro Gly Lys Gly Leu Glu Trp
        35                  40                  45

Ile Gly Glu Ile Tyr His Ser Gly Thr Ser His His Asn Pro Ser Leu
    50                  55                  60

Lys Asn Arg Val Thr Leu Ser Val Asp Lys Ser Lys Asn Gln Phe Ser
65                  70                  75                  80

Leu Lys Leu Asn Ser Met Thr Ala Ala Asp Thr Ala Val Tyr Phe Cys
                85                  90                  95

-continued

```
Thr Arg Leu Asp Phe Asp Ser Pro Leu Gly Met Asp Ala Trp Gly Gln
            100                 105                 110
Gly Thr Thr Val Thr Val Ser Ser
            115                 120

<210> SEQ ID NO 75
<211> LENGTH: 109
<212> TYPE: PRT
<213> ORGANISM: Homo sapiens

<400> SEQUENCE: 75

Asp Ile Val Met Thr Arg Ser Pro Ser Ser Leu Ser Ala Ser Val Gly
1               5                   10                  15
Asp Arg Val Thr Ile Thr Cys Arg Ala Ser Gln Ser Ile Ser Thr Tyr
            20                  25                  30
Leu Asn Trp Tyr Gln Gln Lys Ala Gly Lys Ala Pro Lys Leu Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ser Tyr Ser Thr Pro Arg
                85                  90                  95
Thr Phe Gly Gln Gly Thr Lys Val Glu Ile Lys Arg Ala
            100                 105

<210> SEQ ID NO 76
<211> LENGTH: 110
<212> TYPE: PRT
<213> ORGANISM: Homo sapiens

<400> SEQUENCE: 76

Glu Ile Val Leu Thr Gln Ser Pro Ser Val Ser Ala Ser Val Gly
1               5                   10                  15
Asp Arg Val Thr Ile Thr Cys Arg Ala Ser Glu Asp Val Asn Ser Trp
            20                  25                  30
Leu Ala Trp Tyr Gln Gln Lys Pro Gly Lys Ala Pro Lys Leu Leu Ile
        35                  40                  45
Tyr Gly Ser Thr Asn Leu Gln Gly Gly Val Pro Ser Arg Phe Ser Gly
    50                  55                  60
Arg Gly Ser Gly Thr His Phe Thr Phe Thr Ile Asn Gly Leu Gln Pro
65                  70                  75                  80
Glu Asp Ile Ala Thr Tyr Tyr Cys Lys Tyr Phe Asp Ala Leu Pro Pro
                85                  90                  95
Val Thr Phe Gly Gln Gly Thr Arg Leu Glu Ile Lys Arg Ala
            100                 105                 110

<210> SEQ ID NO 77
<211> LENGTH: 115
<212> TYPE: PRT
<213> ORGANISM: Homo sapiens

<400> SEQUENCE: 77

Asp Ile Val Leu Thr Gln Ser Pro Asp Ser Leu Ala Val Ser Leu Gly
1               5                   10                  15
Glu Arg Ala Thr Ile Asn Cys Thr Ser Ser Gln Ser Leu Leu Tyr Thr
            20                  25                  30
Ser Asn Asn Lys Asn Tyr Leu Thr Trp Tyr Gln Gln Lys Pro Gly Gln
```

```
              35                  40                  45
Pro Pro Lys Leu Leu Ile Tyr Trp Ala Ser Thr Arg Glu Phe Gly Val
         50                  55                  60

Pro Asp Arg Phe Ser Gly Ser Gly Ser Gly Thr Asp Phe Thr Leu Thr
 65                  70                  75                  80

Ile Asn Ser Leu Gln Ala Glu Asp Val Ala Thr Tyr Tyr Cys Gln Gln
                 85                  90                  95

Tyr Ser Asp Pro Pro Thr Phe Gly Gly Thr Lys Leu Glu Ile
            100                 105                 110

Lys Arg Ala
        115

<210> SEQ ID NO 78
<211> LENGTH: 32
<212> TYPE: DNA
<213> ORGANISM: Artificial
<220> FEATURE:
<223> OTHER INFORMATION: primer for PCR
<220> FEATURE:
<221> NAME/KEY: misc_feature
<222> LOCATION: (1)..(5)
<223> OTHER INFORMATION: n is a, c, g, or t

<400> SEQUENCE: 78
nnnnnccatg gcccaggtgc agttggtgga gt                              32

<210> SEQ ID NO 79
<211> LENGTH: 67
<212> TYPE: DNA
<213> ORGANISM: Artificial
<220> FEATURE:
<223> OTHER INFORMATION: primer for PCR
<220> FEATURE:
<221> NAME/KEY: misc_feature
<222> LOCATION: (1)..(5)
<223> OTHER INFORMATION: n is a, c, g, or t

<400> SEQUENCE: 79
nnnnnccgcg gcacgtgggg gtgcttgtgg tgcacgtgca tggggataac cattcagatc  60
ctcttct                                                            67

<210> SEQ ID NO 80
<211> LENGTH: 12
<212> TYPE: PRT
<213> ORGANISM: Artificial
<220> FEATURE:
<223> OTHER INFORMATION: sequence for deriving amino acid sequence for
      binding to porous member

<400> SEQUENCE: 80

Ile Pro Met His Val His His Lys His Pro His Val
 1               5                  10

<210> SEQ ID NO 81
<211> LENGTH: 12
<212> TYPE: PRT
<213> ORGANISM: Artificial
<220> FEATURE:
<223> OTHER INFORMATION: sequence for deriving amino acid sequence for
      binding to porous member

<400> SEQUENCE: 81

Val Ser Pro Met Arg Ser Ala Thr Thr His Thr Val
 1               5                  10
```

<210> SEQ ID NO 82
<211> LENGTH: 357
<212> TYPE: DNA
<213> ORGANISM: Artificial
<220> FEATURE:
<223> OTHER INFORMATION: Variable region of heavy chain A14P-7s4 coding
      DNA

<400> SEQUENCE: 82
caggtgcagt tggtggagtc tggagcagag gtgaaaaagg ccggggagtc tctgaagatc      60
tcctgtaagg gatctggata cagctttccc agttactgga tcaactgggt gcgccagatg     120
cccggcaaag gcctggaatg gatggggatg atctatcctg ctgactctga taccagatat     180
agcccgtcct tccaaggcca cgtcaccatc tcagccgaca gtccatcaa caccgcctac      240 ctgcaatggg ccggcctgaa ggcctcggac accgccatat attactgtgc gagacttgga     300
attggtggga ggtacatgtc tagatggggc caggaaccc tggtcaccgt ctcctca        357

<210> SEQ ID NO 83
<211> LENGTH: 119
<212> TYPE: PRT
<213> ORGANISM: Artificial
<220> FEATURE:
<223> OTHER INFORMATION: Variable region of heavy chain A14P-7s4

<400> SEQUENCE: 83

Gln Val Gln Leu Val Glu Ser Gly Ala Glu Val Lys Lys Pro Gly Glu
1               5                   10                  15

Ser Leu Lys Ile Ser Cys Lys Gly Ser Gly Tyr Ser Phe Pro Ser Tyr
                20                  25                  30

Trp Ile Asn Trp Val Arg Gln Met Pro Gly Lys Gly Leu Glu Trp Met
            35                  40                  45

Gly Met Ile Tyr Pro Ala Asp Ser Asp Thr Arg Tyr Ser Pro Ser Phe
        50                  55                  60

Gln Gly His Val Thr Ile Ser Ala Asp Lys Ser Ile Asn Thr Ala Tyr
65                  70                  75                  80

Leu Gln Trp Ala Gly Leu Lys Ala Ser Asp Thr Ala Ile Tyr Tyr Cys
                85                  90                  95

Ala Arg Leu Gly Ile Gly Gly Arg Tyr Met Ser Arg Trp Gly Gln Gly
                100                 105                 110

Thr Leu Val Thr Val Ser Ser
        115

<210> SEQ ID NO 84
<211> LENGTH: 35
<212> TYPE: DNA
<213> ORGANISM: Artificial
<220> FEATURE:
<223> OTHER INFORMATION: primer for PCR

<400> SEQUENCE: 84
gagcagaggt gaaaaagcca ggggagtctc tgaag                                35

<210> SEQ ID NO 85
<211> LENGTH: 35
<212> TYPE: DNA
<213> ORGANISM: Artificial
<220> FEATURE:
<223> OTHER INFORMATION: primer for PCR

<400> SEQUENCE: 85

```
<210> SEQ ID NO 86
<211> LENGTH: 357
<212> TYPE: DNA
<213> ORGANISM: Artificial
<220> FEATURE:
<223> OTHER INFORMATION: Variable region of heavy chain PFER-7s4 coding
      DNA

<400> SEQUENCE: 86
caggtgcagt tggtggagtc tggagcagag gtgaaaaagc caggggagtc tctgaagatc      60
tcctgtaagg gatctggata cagctttccc agttactgga tcaactgggt gcgccagatg     120
cccggcaaag gcctggaatg gatggggatg atctatcctg ctgactctga taccagatat     180
agcccgtcct tccaaggcca cgtcaccatc tcagccgaca gtccatcaa caccgcctac      240 ctgcaatggg ccggcctgaa ggcctcggac accgccatat attactgtgc gagacttgga     300
attggtggga ggtacatgtc tagatggggc cagggaaccc tggtcaccgt ctcctca        357

<210> SEQ ID NO 87
<211> LENGTH: 119
<212> TYPE: PRT
<213> ORGANISM: Artificial
<220> FEATURE:
<223> OTHER INFORMATION: Variable region of heavy chain PFER-7s4

<400> SEQUENCE: 87

Gln Val Gln Leu Val Glu Ser Gly Ala Glu Val Lys Lys Pro Gly Glu
1               5                   10                  15

Ser Leu Lys Ile Ser Cys Lys Gly Ser Gly Tyr Ser Phe Pro Ser Tyr
            20                  25                  30

Trp Ile Asn Trp Phe Arg Gln Met Pro Gly Lys Glu Arg Glu Trp Met
        35                  40                  45

Gly Met Ile Tyr Pro Ala Asp Ser Asp Thr Arg Tyr Ser Pro Ser Phe
    50                  55                  60

Gln Gly His Val Thr Ile Ser Ala Asp Lys Ser Ile Asn Thr Ala Tyr
65                  70                  75                  80

Leu Gln Trp Ala Gly Leu Lys Ala Ser Asp Thr Ala Ile Tyr Tyr Cys
                85                  90                  95

Ala Arg Leu Gly Ile Gly Gly Arg Tyr Met Ser Arg Trp Gly Gln Gly
            100                 105                 110

Thr Leu Val Thr Val Ser Ser
        115

<210> SEQ ID NO 88
<211> LENGTH: 33
<212> TYPE: DNA
<213> ORGANISM: Artificial
<220> FEATURE:
<223> OTHER INFORMATION: primer for PCR

<400> SEQUENCE: 88
ttactggatc aactggttcc gccagatgcc cgg                                    33

<210> SEQ ID NO 89
<211> LENGTH: 33
<212> TYPE: DNA
<213> ORGANISM: Artificial
<220> FEATURE:
<223> OTHER INFORMATION: primer for PCR
```

-continued

```
<400> SEQUENCE: 89
ccgggcatct ggcggaacca gttgatccag taa                           33

<210> SEQ ID NO 90
<211> LENGTH: 33
<212> TYPE: DNA
<213> ORGANISM: Artificial
<220> FEATURE:
<223> OTHER INFORMATION: primer for PCR

<400> SEQUENCE: 90
cagatgcccg gcaaagaact ggaatggatg ggg                           33

<210> SEQ ID NO 91
<211> LENGTH: 33
<212> TYPE: DNA
<213> ORGANISM: Artificial
<220> FEATURE:
<223> OTHER INFORMATION: primer for PCR

<400> SEQUENCE: 91
ccccatccat tccagttctt tgccgggcat ctg                           33

<210> SEQ ID NO 92
<211> LENGTH: 31
<212> TYPE: DNA
<213> ORGANISM: Artificial
<220> FEATURE:
<223> OTHER INFORMATION: primer for PCR

<400> SEQUENCE: 92
gcccggcaaa gaagggaat ggatggggat g                              31

<210> SEQ ID NO 93
<211> LENGTH: 31
<212> TYPE: DNA
<213> ORGANISM: Artificial
<220> FEATURE:
<223> OTHER INFORMATION: primer for PCR

<400> SEQUENCE: 93
catccccatc cattccctgc ctttgccggg c                             31

<210> SEQ ID NO 94
<211> LENGTH: 5
<212> TYPE: PRT
<213> ORGANISM: Artificial
<220> FEATURE:
<223> OTHER INFORMATION: linker

<400> SEQUENCE: 94

Gly Gly Gly Gly Ser
1               5
```

STRUCTURE AND METHOD FOR RELEASING SUBSTANCE THEREFROM

This application is a divisional of application Ser. No. 11/094,132, filed Mar. 31, 2005, the contents of which are incorporated herein by reference.

BACKGROUND OF THE INVENTION

1. Field of the Invention

The present invention relates to a structure comprising a porous body, a capping member, and a connecting member for connecting the porous body and the capping member, and relates also to a method for releasing a substance kept by the capping member in the porous body.

2. Related Background Art

Many investigations are being made on stimulation-responsive materials which function by changing a shape or a property thereof in response to an external stimulation such as light irradiation, electric field application, and chemical substance addition; or an environmental change such as a temperature change, and a pH change. The function of the stimulation-responsive material can be controlled from outside by utilizing the property, and is promising in various application fields, such as drug delivery.

Generally, a drug is dosed into a body by injection, oral administration, painting, or a like method, and the dosed drug circulates in the body to reach a target site. In these dosing method generally, the drug can diffuse to a portion other than the targeted diseased portion or may be absorbed or decomposed in a digestive tract or other tract undesirably, reaching the diseased portion finally in a quantity (concentration) much smaller than the dosed quantity. Therefore, the drug is dosed in a quantity larger than that actually required.

To solve the above problem, various measures are taken, including modification of a portion of the drug compound relating to the absorption or decomposition without lowering the drug effect, use of a drug carrier, and so forth. The drug carrier carries a drug selectively to a targeted diseased portion or an objective matter such as internal organs, tissues, cells, and pathogens. This technique employing a drug carrier is called a drug delivery system (hereinafter referred to as "DDS"). This DDS technique can increase the treatment effect of the drug, and can decrease the drug dose to lower the adverse effect of the drug advantageously. As the drug carrier, liposomes, lipid microsheres, and the like are being investigated.

A liposome is a spherical vesicle of lipid having a hydrophilic portion and a hydrophobic portion, constituted of a bilayer with the hydrophobic groups placed inside to be stable to an outside water environment. A liposome having a stable bilayer structure can be formed by dissolving a natural lipid such as lecithin and cholesterol in an organic solvent and dispersing it in water by ultrasonic treatment or a like method. In the liposome forming process, a drug to be carried can be enclosed in the liposome, A drug which is a hydrophobic substance is held in the inside of the bilayer whereas a drug which is hydrophilic is held in the inside water phase enclosed by the bilayer.

Lipid microspheres can be prepared by suspending a drug-containing soybean oil and lecithin in water, having the lecithin on the surface and the drug-containing soybean oil enclosed therein. Medical formulations comprising such lipid microspheres enclosing an anti-inflammatory drug are used in clinical treatment. Japanese Patent Application Laid-Open No. H05-221852 discloses a method for forming lipid microspheres containing a fatty acid ester and having fine particle surfaces by dissolving a fat-soluble anticancer agent in the fatty acid and homogenizing the fatty acid ester solution with a surfactant such as a phospholipids. However, the liposome structure can readily be destroyed by contact with a lipid or protein in blood, being not stable in vivo for a long time. For stabilization, modification of the liposome by polyethylene glycol (PEG) or a polysaccharide is investigated. However, the stability is not satisfactory yet. Further, to use the lipid microsphere, the drug should be fat-soluble, but fat-soluble drug is not stable in the blood similarly as the liposome, and is liable to migrate to reticuloendothelial system. The liposome needs to be improved more for use as the drug carrier.

For improving the stability of the aforementioned drug carriers in the blood, a report is presented which utilizes a block copolymer constituted of polyethylene glycol as the hydrophilic portion and polyamino acid as the hydrophobic portion to form a micelle-like structure in an aqueous solution or a phosphate buffer solution (Drug Delivery System, Vol. 6(2), pp77, 1991). This block copolymer is capable of forming a micelle-like stable structure in an aqueous solution or an aqueous phosphate buffer solution. A drug like an anti-cancer agent is enclosed in this structure for stabilization in the blood.

U.S. Pat. No. 3,854,480 discloses a drug delivery system which releases a drug at a controlled rate for a long term. This system employs a structure constituted of a film and a drug-containing core, the film being composed of a polymer such as polyethylene and an ethylene-vinyl acetate copolymer, and the drug-containing core being composed of a matrix of polymethylsiloxane or the like containing a drug dispersed therein. The drug is released to outside from the core through the film by diffusion.

The above disclosures do not teach a technique for releasing the drug selectively to the targeted diseased portion. For more effective medical treatment and lower side effect of the drug, a drug carrier is demanded to be developed which has capability of controlling the drug release at a targeted site as well as the stability after administration in the blood and other portion of the body and on the body surface.

To meet such demand, a technique is disclosed which encloses a drug or a chemical compound in a silica type porous material stable in the body fluid like blood and releases the compound with control by outside stimulation (J. Am. Chem. Soc., Vol. 125, pp4451, 2003). In the disclosed technique, the material for enclosing the drug is mesoporous silica (MCM-41) having an average particle size of 200 nm, and an average pore diameter of 2.3 nm (hereinafter referred to as a "silica structure") modified by 2-(propyldisulfanyl) ethylamine. By this technique, the silica structure is immersed in an aqueous solution of ATP and vancomycin, and thereto CdS (average particle size: 2.0 nm) is added which has been modified by acetic acid thiol to cause bridging by chemical bonding between the amino groups on the surface of the silica structure and the carboxyl groups of the CdS surface to cap the silica structure to enclose the drug. The compound enclosed in the silica structure is released by treatment with a reducing agent such as DTT and mercaptoethanol to cleave the S—S bond of the disulfanyl groups to remove the CdS from the mesoporous silica.

A report (J. Material. Biomed. Mater. Res. 51, pp293 (2000)) discloses a technique for destroying nano particles constituted of cores of a hydrogel of an N-isopropylacrylamide-acrylamide copolymer (NIPAAm-AAm) coated with gold by swelling of the NIPAAm-AAm core by absorption of near infrared light of 800 to 1200 nm and a resulting photothermal conversion reaction. This report suggests also possibility of drug release, by light response, from NIPAAm-AAm containing a drug suspended or dissolved therein. The near infrared light in the range from 800 to 1200 nm penetrates a human tissue but is harmless. However, the core material, NIPAAm-AAm, is not completely safe to the tissue of the human body.

In the aforementioned methods, the silica structure enclosing a drug and a reducing agent are allowed to coexist, or a gold-coated fine particulate NIPAAm-AAm is used for the controlled release of the drug. However, the localization of the reducing agent in the diseased portion has technical problems in the method and the safety to be solved.

SUMMARY OF THE INVENTION

The present invention has been made to satisfy the demand for a structure for controlled release of a drug or a like substance. The present invention intends to provide a structure which is capable of surely controlling release of a substance like a drug at a prescribed site.

After comprehensive investigation to solve the above problems, the inventors of the present invention have found a structure described below.

According to an aspect of the present invention, there is provided a structure comprising at least a porous body holding a substance releasably, comprising a capping member for keeping the substance inside the pore and/or on at least a part of the entire surface of the porous body, and a connecting member for connecting the porous body and the capping member separably, the connecting member comprising a biopolymer compound.

The connecting member preferably has a first site for bonding to the porous body and a second site for bonding to the capping member.

The site of the connecting member for bonding to the capping member preferably comprises at least a portion of an antibody variable region capable of bonding to the capping member.

In the structure, gold is preferably contained at least a part of the surface of the capping member, and the bonding site of the connecting member is preferably capable of bonding to the gold. The bonding site of the connecting member for bonding to the capping member preferably comprises one or more amino acid sequence selected from the group consisting of amino acid sequences of SEQ ID NO:1 to 57.

The bonding site of the connecting member for bonding to the capping member preferably comprises one or more amino acid sequence selected from the group consisting of amino acid sequences derived from the amino acid sequences SEQ ID NO:1 to 57 by deletion, substitution or addition of one or more amino acids.

In the above structure, the bonding site of the connecting member for bonding to the porous body preferably comprises a peptide capable of bonding to the porous body. At least a part of the surface of the porous body preferably contains at least one of metals and metal oxides, and the bonding site of the connecting member to the porous body is preferably capable of bonding to the part of the surface of the porous body containing at least one of metals and metal oxides. Alternatively, at least a part of the surface of the porous body contains silicon oxide, and the bonding site of the connecting member to the porous body is preferably capable of bonding to the part containing the silicon oxide. The bonding site of the connecting member for bonding to the porous body comprises two or more amino acid sequences selected from the group consisting of (1) amino acid sequence SEQ ID NO:80, and (2) amino acid sequences derived by deletion, substitution or addition of one or more amino acid from or to amino acid sequence SEQ ID NO:81.

The bonding of the connecting member to at least one of the capping member and the porous bodies is preferably broken by external stimulation to render releasable the substance kept by the capping member in the porous body.

According to another aspect of the present invention, there is provided a method for releasing a substance from the structure set forth in above, comprising the steps of:

applying stimulation from outside to the structure, and cleaving at least one of the bonding between the connecting member and the capping member and the bonding between the connecting member and the porous member to make the substance releasable from the structure. The stimulation is preferably a physical action. The physical stimulation is preferably at least one of light and a magnetic field, and the physical stimulation causes a change of temperature of the capping member, and the temperature change cleaves the bonding between the capping member and the connecting member.

The structure of the present invention is effective as mentioned below. Firstly, in holding one or more substances in the structure, the feature of a porous body having a large surface area per unit volume can be utilized most effectively for holding the substance to be released on at least a part of the entire surface comprising the outside surface and inside surface of pore wall, preferably at least on the inside surface of the pore and the pore opening periphery. Secondly, spontaneous diffusion of the substance held by the porous body can be prevented by a capping member. Thirdly, the connection of the capping member with the porous body can be stabilized by physical or chemical connection between the porous body and the capping member surface.

BRIEF DESCRIPTION OF THE DRAWINGS

FIG. 1 illustrates schematically a structure of the present invention, and release of a compound from the structure.

DETAILED DESCRIPTION OF THE PREFERRED EMBODIMENTS

Figure 2A:
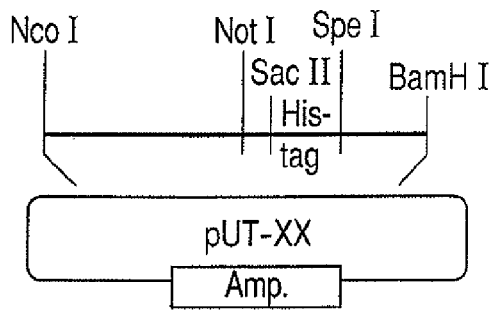
FIGS. 2A, 2B, 2C, 2D, 2E, and 2F illustrate examples of preparation of a vector for production of a biopolymer compound.

The preferred embodiments of the present invention are explained below in detail by reference to drawings. (Incidentally, the embodiments not experimentally practiced are described later.)

(Structure)

The structure of the present invention holds one or more substances to be releasable. The structure comprises a porous body, a capping member, and a connecting member for connecting the porous body and the capping member physically or chemically, the connecting member comprising an organic compound comprising a biopolymer compound.

The size of the structure depends on the size of the porous body as the base material described later, and can be selected and designed for the use of the structure. For example, for use for DDS, the diameter or maximum length of the particle is preferably not more than 200 nm; for delivery to finer blood capillary, preferably not more than 50 nm. The lower limit of the size is not specially limited, but the diameter or maximum length of the particle is not less than 5 nm. The releasable substance is held by at least one of an outside surface of the porous body, an inside space of the pores, and an inside surface of the porous body, namely an inside wall of the pore. The substance is held preferably on the outside surface or the inside surface, more preferably at least on the inside surface and opening periphery of the pore.

(Porous Body)

The porous body for the structure of the present invention has a large surface area per unit volume, namely a specific surface area, for achieving the effect of the present invention. The pores of the porous body are open to the outside of the structure. The shape of the pore is selected to be suitable for the substance to be held releasably in the pore and for the outside environment, namely properties of a liquid or solution suspending or dissolving the substance. The pore preferably penetrates through the porous body. The diameter of the pore ranges preferably from 1 nm to 10 µm, more preferably from 50 nm to 1000 nm.

The constituting material of the porous body is selected suitably from known materials. The material is selected from the group of metals, metal oxides, insoluble inorganic salts, inorganic semiconductors, organic semiconductors, and organic polymer compounds, and composites thereof; the organic polymer compounds including natural polymer compounds, synthetic polymer compounds, plastics, pulp, woven cloths, and nonwoven cloths; and composites thereof. The metals include gold, silver, platinum, aluminum, and copper. The metal oxides include silicon oxide, alumina, titanium oxide, zinc oxide, magnetite, ferrite, NbTa composite oxide, $WO_3$, $In_2O_3$, InSnO, $MoO_3$, $V_2O_5$, and $SnO_2$. The insoluble inorganic salts include hydroxyapatite, and calcium phosphate gel. The organic polymer compounds include polymers and copolymers produced by polymerizing or copolymerizing a polymerizable monomer or monomers selected from the group of known styrene monomers such as styrene, α-methylstyrene, and β-methylstyrene; methacrylate monomers such as methyl acrylate, and ethylacrylate; methylene aliphatic monocarboxylic acid esters; vinyl esters such as vinyl acetate, and vinyl propionate; vinyl ethers such as vinyl methyl ether; and vinyl ketones such as vinyl methyl ketone.

Further, the structure may be formed from any of the materials including films constituted of a polymer such as polyethylene terephthalate (PET), diacetate, triacetate, cellophane, celluloid, polycarbonate, polyimide, polyvinyl chloride, polyvinylidene chloride, polyacrylate, polyethylene, polypropylene, and polyesters; porous polymer films of polyvinyl chloride, polyvinyl alcohol, acetylcellulose, polycarbonate, nylon, polypropylene, polyethylene, Teflon, and the like; wood plates; glass plates; silicon substrates; cloths produced from cotton, rayon, acrylates, silk, polyesters or the like; and paper sheets of wood-free paper, medium quality paper, art paper, bond paper, regenerated paper, baryta paper, cast-coated paper, corrugated paper, and resin-coated paper, but is not limited thereto.

Among the above materials, metal oxides are preferred as the material for the drug carrier in consideration of stability in the body fluid, the biocompatibility, and the production cost of the porous body. The metal oxides include silicon oxide, aluminum oxide, iron oxide, and ferrite. When the release of the material from the structure is controlled by light/magnetism, silicon oxide is the most suitable as the porous body constituting material which does not absorb the light or is not affected by the magnetism.

The porous body may have any constitution shown below.

Figure 14A:
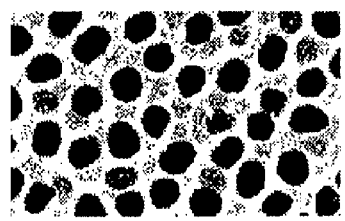
FIGS. 14A, 14B, 14C, 14D, 14E, 14F, 14G, and 14H illustrate respectively a fine structure: a porous structure, an opal structure, a reversed opal structure, a columnar structure, a convexed structure, a concaved structure, a projecting structure, and a fibrous structure.

Hollow column construction: many cylindrical hollows of any shape are arranged (FIG. 14A)

Figure 14B:
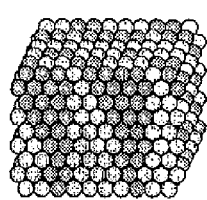

Porous construction: many pores of any shape are formed at random (FIG. 14B)

Figure 14C:
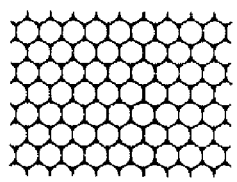

Opal constitution: spherical matters are closely packed (FIG. 14C)

Figure 14D:
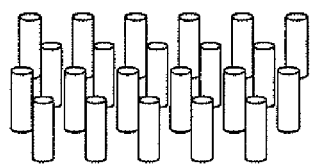

Reversed opal constitution: material/pore is reversed in the opal constitution (FIG. 14D)

Figure 14E:
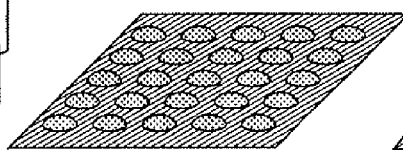
Figure 14F:
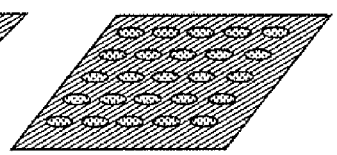
Figure 14G:
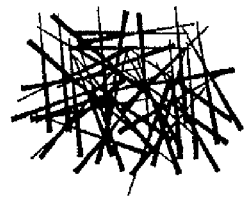
Figure 14H:
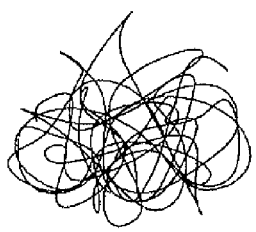

Concave constitution: many concaves are formed in the substrate (FIG. 14E)

The porous body may be provided on a suitable supporting base plate, or may be an independent body. The supporting base plate may be made of a known material including metals, metal oxides, plastics, and composites thereof.

The porous body may be formed by any working method suitable for the material selected as above. The working method includes photolithography, etching, sand blasting, and FIB working. When aluminum is selected as the material, the porous body can be formed by an electrochemical method such as anodation. When silicon oxide is selected as the material, the porous body can be formed by a sol-gel method. This method enables formation of porous body having an average pore diameter ranging from 2 to 20 nm, and an average particle diameter of about 200 nm. An example of this method is described.

An alkoxysilane solution containing a surfactant is applied under acidic conditions to form a coating layer. The layer is treated at 35° C. for 20 hours to allow the reaction to proceed, and is further heated at 80° C. for 48 hours. Thereby a silicon oxide layer is formed which contains a surfactant phase distributed in a net state. Then the surfactant phase distributed in the layer is eliminated by heating at 500° C. for 6 hours. The resulting porous material layer has a porous constitution having pores of the diameter ranging from 1 nm to 1000 nm at the region of the eliminated surfactant phases, The surfactant may be eliminated, other than the above heating method, by treatment with an organic solvent. The method is selected to be suitable depending on the properties, such as heat resistance and solvent resistance, of the base plate employed.

(Capping Member)

The capping member keeps the compound in the structure of the present invention not to disappear by spontaneous diffusion or a like process, and releases the compound outside on receiving an external signal such as light and a magnetic field change. On receiving light or a magnetic field change, the capping member causes preferably a temperature change at the periphery thereof.

Suitable materials for the capping member includes metals such as gold, silver, copper, platinum, zinc, aluminum, and silicon; magnetizable metals such as iron, cobalt, and nickel; and oxides thereof. Of these, preferred are gold, silver, copper, and platinum which are capable of converting readily the absorbed light or the magnetic field to heat, but are not limited thereto.

The size of the capping member is not limited. However, when the capping member is much smaller than the pore diameter of the porous body, the substance held by the porous body can diffuse through a gap between the pore wall face and the capping member. On the other hand, when the capping member is much larger than the porous body, the capping member covers incompletely the openings of the plural pores not to function sufficiently as the capping member. In consideration of the above preferred pore diameter of 1-10 nm, or considering the diameter of the porous body, the diameter of the capping member ranges preferably from 1 to 100 nm, more preferably from 2 to 50 nm.

From the aforementioned reasons, gold is the most suitable as the material of the capping member. For example, a fine particle constituted of silica as the core and coated with gold on the surface and having particle diameters ranging from 1 to 100 nm generates heat on absorption of light of 800 to 1200 nm. The generated heat can be utilized to disconnect the biopolymer compound comprised in the connecting member and the capping member to separate the capping member from the porous body.

(Biopolymer Compound)

The biopolymer comprised in the connecting member connects physically or chemically the capping member to the porous body. The biopolymer has preferably a bonding site for bonding to the porous body surface, and a bonding site for bonding to the capping member. More preferably at least one of the bonding sites comprises at least a part of the variable region of an antibody. The "antibody" in the present invention includes antibodies produced from lymphoid cells of a vertebrate, and proteins which have an amino acid sequence derived by deletion, substitution, or addition of an amino acid constituting the antibody without losing the desired function as the antibody and by keeping the relation to the original antibody in the constitution and function. The bonding site of the connecting member which is capable of bonding to the porous body surface and/or the capping member surface may be a fragment, domain, or part (hereinafter referred to as an "antibody part") of the antibody. The antibody part which can be a bonding site is exemplified by variable regions $V_H$ and $V_L$, and composites thereof, the composites being exemplified by a single chain $F_V$ ($_{sc}F_V$) derived from $F_V$, $V_H$, and $V_L$ bonded through a peptide composed of several amino acids, and a portion thereof.

In the case where gold is contained in at least a portion of the capping member surface and the connecting member has a site to bond to the gold portion, the connecting member may comprise a gold-bonding protein. The gold-binding protein may comprise an antibody part, and may comprise Fab', (Fab')$^2$, Fd, $F_V$ and a part thereof.

In the case where the $_{sc}F_V$ is used for constituting the connecting member, a linker constituted of one or more amino acids is preferably placed between $V_H$ and $V_L$ (no particular arrangement order) forming the $_{sc}F_V$. The residue length of the amino acid linker should be designed not to prevent the formation of the necessary constitution for bonding between the $V_H$ or $V_L$ and the antigen. The length of the amino acid linker is generally 5 to 18 residues: the length of 15 residues is most widely employed or investigated.

The aforementioned constitution part of the connecting member can be obtained by a genetic engineering technique.

Figures 4A, 4B, 4C, 4D:
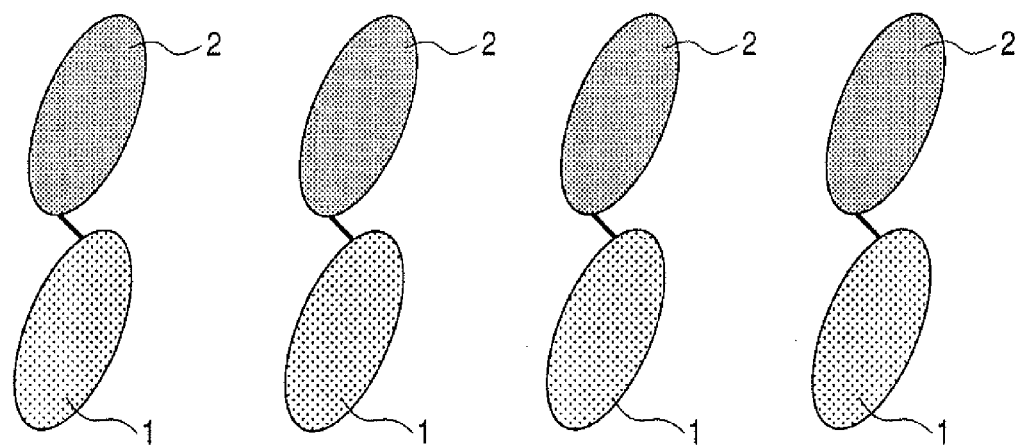
FIGS. 4A, 4B, 4C and 4D illustrate schematically a constitution of a gold-bonding protein.
Figure 5:
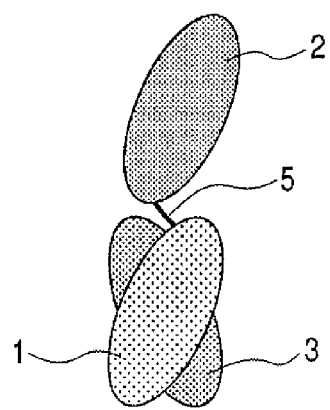
FIG. 5 illustrates schematically a constitution of a gold-bonding protein.
Figure 6:
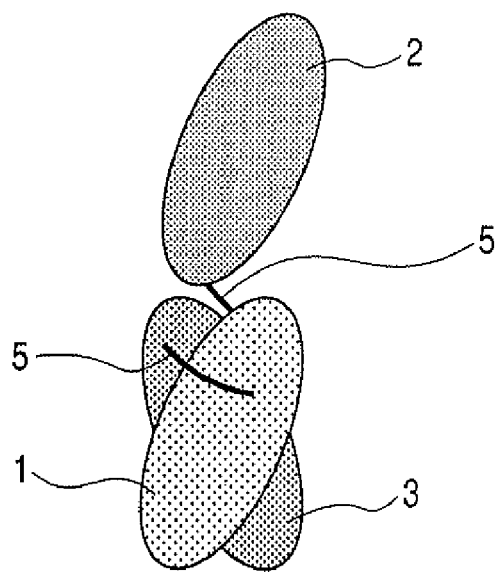
FIG. 6 illustrates schematically a constitution of a gold-bonding protein.

The bonding site of the biopolymer compound for bonding to the porous body surface and the bonding site thereof for bonding to the capping member may be respectively an antibody part; one site may be an antibody part and the other site may be a peptide chain constituted of 5 or more amino acids; or the both sites may be respectively a peptide chain constituted of 5 or more amino acids. In the description below, the antibody domain constituting the antibody part serving as a bonding site to the capping member surface is referred to as a first domain, and the antibody domain constituting an antibody part serving as a bonding site to the porous body surface is referred to as a second domain. FIGS. 4A to 4D illustrate the bonding sites which are respectively an antibody domain. In each of the drawings, the reference numeral 1 denotes the first domain, and the reference numeral 2 denotes the second domain. In FIG. 4A, the first domain and the second domain are both $V_H$; in FIG. 4B, the first domain is $V_H$ and the second domain is $V_L$; in FIG. 4C, the first domain is $V_L$, and the second domain is $V_H$; and in FIG. 4D, the first domain and the second domain are both $V_L$. The bonding sites of the first domain and the second domain are preferably not complementary. In the connecting member, between the first domain and the second domain, a constituting part other than a polypeptide chain may be provided; the both domains may be joined directly; or the both domains may be joined with interposition of a polypeptide. Joining with a peptide is preferred for simplification in expression of the functions and in production process. The interposed peptide may be a linker constituted of one or more amino acids. The linker is preferably constituted of 1 to 10 amino acids, more preferably 1 to 5 amino acids, When the linker has a length of 11 to 15 amino acids, the freedom of the relative position of the domains increases to cause complementary bonding between the domains (scFv formation), which can prevent joining to the capping member and the porous body. Further, the linker may have an embodiment that the linker is designed in a manner that the two-dimensional structure allows each of the domains to permit each other to assume forms capable of easily bonding a target material to be bonded with the domains.

The biopolymer compound having the first and second domains may have another domain containing at least a portion of $V_H$ and/or at least a portion of $V_L$, namely a third domain and/or fourth domain. The third domain forms a composite with the first domain, and the fourth domain forms a composite with the second domain. For example, when the first domain is $V_H$, the third domain is $V_L$ capable of forming $F_V$ with the first domain, and the resulting composite forms a bonding site in combination of the first domain and the third domain for bonding to a capping member surface. Similarly, when the second domain is $V_L$, the fourth domain is $V_H$ capable of forming $F_V$ with the second domain, and the resulting composite forms a bonding site in combination of the second domain and the fourth domain for bonding to a porous body surface.

FIGS. 5, 6, 7, 11, 12, and 13 illustrate schematically the state of the composite of the first domain with the third domain. FIGS. 8, 9, 10, 11, 12, and 13 illustrate schematically the state of the composite of the second domain with the fourth domain. The formation of the composite can stabilize the constitution to retard drop of the function by constitution change. Such a composite forms preferably a bonding site in combination for bonding to the capping member surface or the porous body surface. The formation of the bonding site in combination of the domains can be effective in improving the bonding properties such as increase of the bonding rate, retardation of the dissociation rate, and so forth. In such a manner, the constitution can be selected for bonding the domain and domain composite to the porous body surface and the capping member surface.

Figure 7:
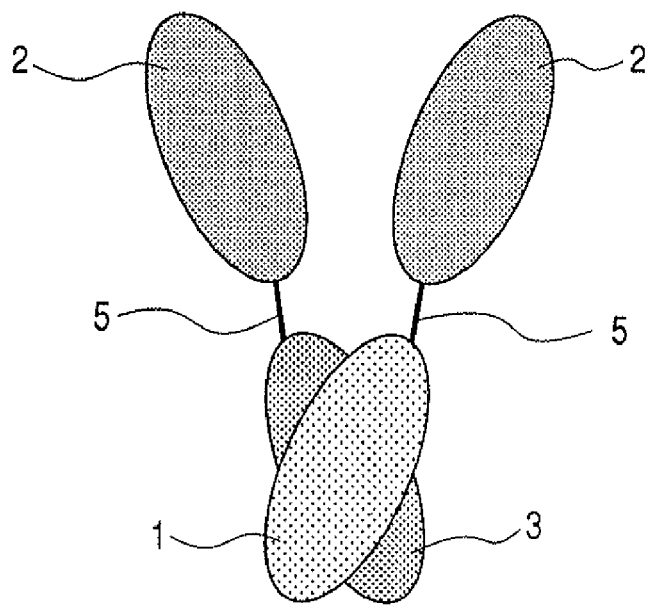
FIG. 7 illustrates schematically a constitution of a gold-bonding protein.
Figure 8:
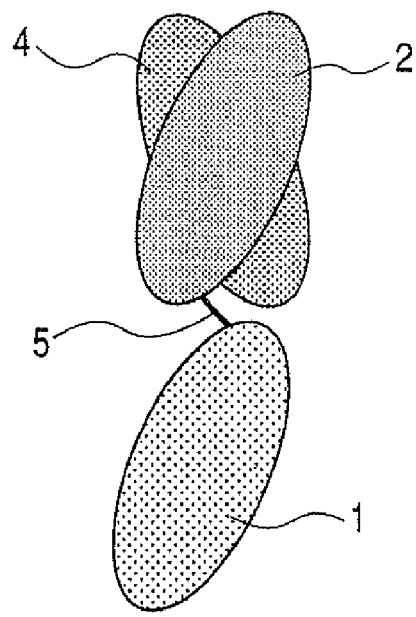
FIG. 8 illustrates schematically a constitution of a gold-bonding protein.
Figure 9:
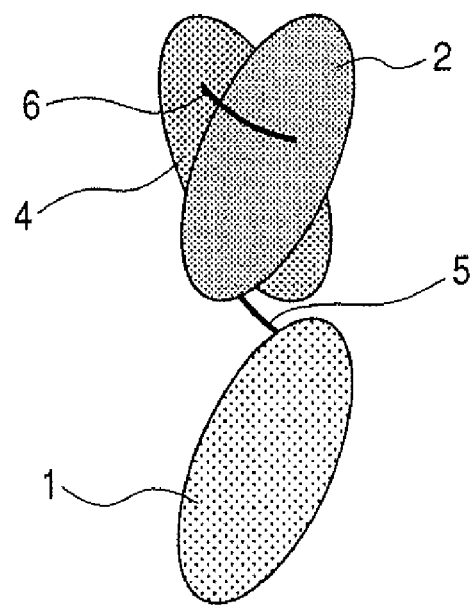
FIG. 9 illustrates schematically a constitution of a gold-bonding protein.
Figure 10:
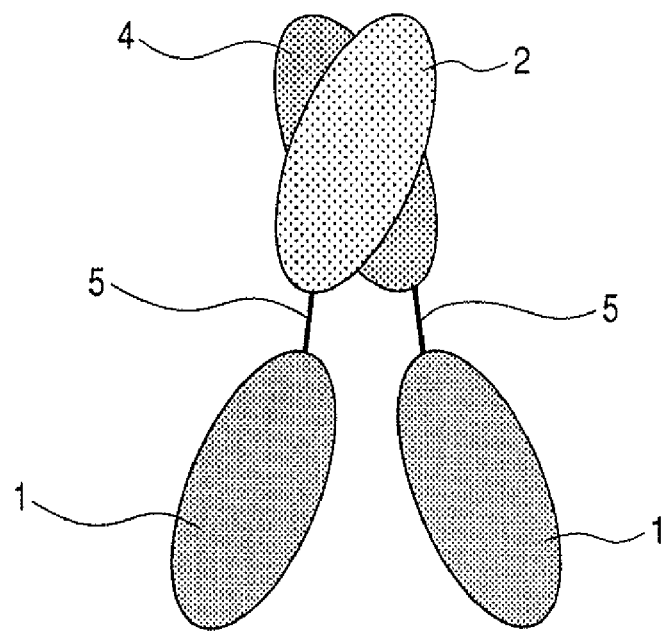
FIG. 10 illustrates schematically a constitution of a gold-bonding protein.
Figure 11:
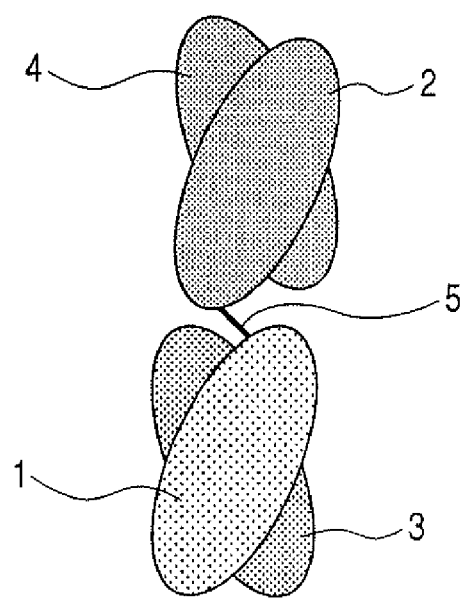
FIG. 11 illustrates schematically a constitution of a gold-bonding protein.
Figure 12:
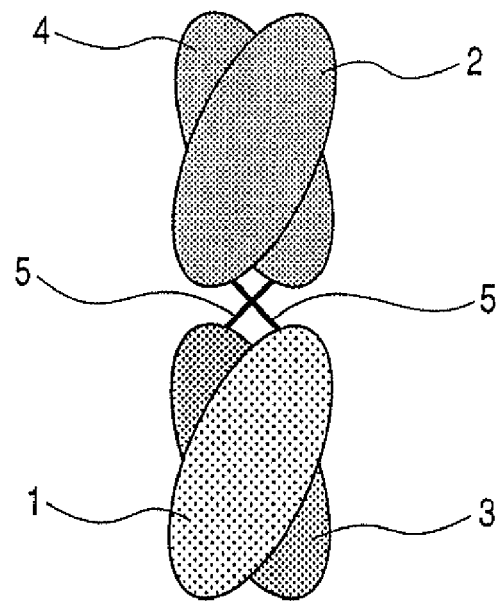
FIG. 12 illustrates schematically a constitution of a gold-bonding protein.
Figure 13:
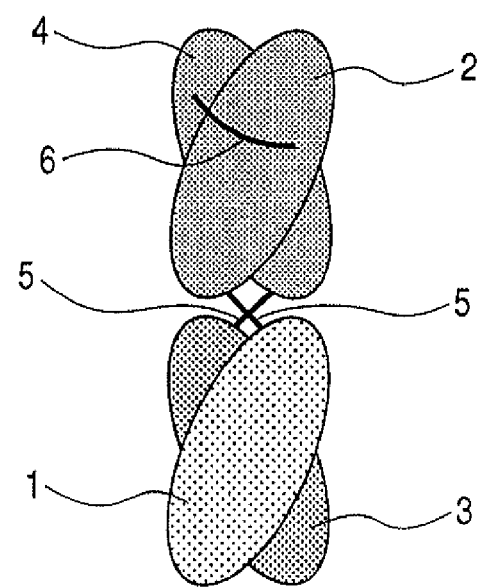
FIG. 13 illustrates schematically a constitution of a gold-bonding protein.

The constitution shown schematically in FIG. 7 can be employed in which a polypeptide chain comprises the first domain and the second domain and in which the third domain forms a composite with the first domain. With this constitution, $F_V$ or an $F_V$-like composite formed from the first domain and the third domain bonds to the capping member surface, and the bonding of the two second domains to the porous body serves as an anchor biting the porous body. Similarly, the constitution shown schematically in FIG. 10 can be employed which is constituted of a polypeptide chain comprising the first domain and in which the second domain and the fourth domain forms composite with the first domain. With this constitution, $F_V$ or an $F_V$-like composite formed from the second domain and the fourth domain bonds to the porous body surface, and the bonding of the two first domains to the capping member serves as an anchor biting the capping member body.

The pair of the domains forming the composite may be respectively an independent polypeptide chain, or may be linked together directly by a linker. The linker for linking the domains of the composite having bonding sites for bonding to the capping member and the porous body has preferably a chain of 1 to 10 amino acids, more preferably 1 to 5 amino acids by the same reason as the aforementioned linker for connecting the domain having a bonding site to the capping member and the domain having a bonding site to the porous body, but may be longer if necessary. For example, in the case of FIG. 13, the first and second domains, and the third and fourth domains may be respectively linked by 1 to 5 amino acids, and the second and third domains may be linked by 15 to 25 amino acids. FIG. 6 illustrates schematically a polypeptide chain in which the first and third domains are linked by a linker. FIGS. 9 and 13 illustrate schematically a polypeptide in which the second and fourth domains are linked by a linker. In FIGS. 6, 9, and 13, the first and second domains are linked by a linker, and further in FIG. 13, the third and fourth domains are linked by a linker. Therefore, sequences of polypeptide chains are formed: second-first-third domains in FIG. 6, first-second-fourth domains in FIG. 9, and first-second-fourth-third domains in FIG. 13. The arrangement of the domains in the single-stranded polypeptide can be selected suitably for intended properties such as properties for bonding to gold or a target, and long-term stability of the gold-bonding protein.

Further, the biopolymer compound constituted of an antibody fragment and having the aforementioned domain composite for forming a bonding site (e.g., the first and third domains, and the second and forth domains) can be modified genetically at a portion which does not affect greatly the intended bonding property. For example, a disulfide bond is formed at the bonding interface between the domains by introducing a cysteine residue at the interface between the domain composite (e.g., the first and third domain, or the second and fourth domains). Otherwise, two cysteine moieties are introduced in the linker to promote formation of a domain composite for forming the same bonding sites or for improving the stability.

The variable region of the antibody for use as the connecting member has preferably at least one of the amino acid sequences: SEQ ID NO:1 to SEQ ID No:57. The variable region may have also an amino acid sequence or sequences selected from the amino acid groups obtained by deletion, substitution, or addition of one or more amino acids to or from any of the above 57 amino acid sequences, provided that the connecting member can function as intended. The amino acid sequences of the variable region of the antibody having the sequence of SEQ ID NO:1 to SEQ ID NO:57 are exemplified by the sequences SEQ ID NO:58 to SEQ ID NO:77. In this connection, SEQ ID NO:58 to SEQ ID NO:77 are denoted by the following names in the present specification in a manner as "58: 7s1" which means SEQ ID NO:58 is denoted by a name 7s1: 58: 7s1, 59: 7s2, 60: 7s4, 61: 7s7, 62: 7s8, 63: 7p2, 64: 7p3, 65: 7p4, 66: 7p7, 67: 7p8, 68: 10s1, 69: 10s2, 70: 10s3, 71: 10s4, 72: 10s5, 73: 10p1, 74: 10p2, 75: No. 4, 76: No. 7, and 77: No. 10.

A biopolymer compound like this can be prepared genetically as a protein. The biopolymer compound can be obtained as a fused protein by introduction of a nucleic acid coding for the biopolymer compound to an expression vector, expression, and purification. The protein may be prepared as a single strand polypeptide chain. In formation of a single stranded polypeptide, for example, a nucleic acid for coding for a peptide affinitive to a substrate is introduced to a 5'-terminal (or 3' terminal) of a nucleic acid for coding a variable region of an antibody to obtain a nucleic acid for coding for a protein fused with a substrate-affinitive peptide at an N-terminal (or C-terminal) of the variable region. In this case, it is also possible to insert a nucleic acid sequence which codes a amino acid sequence of the above linker between the nucleic acid sequence coding the antibody fragment and the nucleic acid sequence coding the affinitive peptide chain. Further, the biopolymer compound may be constituted of a composite of a plural polypeptide chains. The constitution of the protein is not limited provided that the necessary function of the connecting member is not impaired.

In the case where the connecting member of the present invention has an antibody fragment and an affinitive peptide as the bonding sites respectively to the porous body and the capping member. For example, a protein can be formed by fusion of the above affinitive peptide to a variable region of an antibody, or an N-terminal or C-terminal of a composite of the antibody. The peptide chain affinitive to the capping member can be selected in consideration of the bonding ability by design by calculation and screening by a peptide presentation method such as a known phage display method. Otherwise, the selection can be made by preparing a candidate library with reference to known amino acid sequences (Nature Materials, Vol. 1, 2, pp577, 2003) and screening them. For the porous body composed of a silicon oxide type material, especially SBA-15, suitable are SEQ ID NO:80 to SEQ ID NO:81.

In the same manner as above, in a combination of ${}_{SC}F_V$ moieties forming a bonding site (e.g., the first domain and the third domain; or the second domain and the fourth domain mentioned above), a part thereof which does not affect the intended bonding properties may be genetically modified. For example, the modification can be made by formation of a disulfide linkage at the joining interface between ${}_{SC}F_V$ moieties: a cysteine residue is introduced to the bonding interface between the portions of ${}_{SC}F_V$ (e.g., the first domain and the third domain; or the second domain and the fourth domain); or two cysteine residues are introduced to the linker to assist formation of $_{sc}f_V$ having the same bonding site for stabilization.

The protein-expressing vector can be designed and constructed by incorporating construction for expressing gene for coding for a biopolymer compound like a known promoter corresponding to a selected host cells. When Escherichia coli is used as the host cells, the decomposition by a protease can be retarded by removing a protein or its constituent, a foreign genetic product, quickly to the outside of the cell. If the foreign genetic product is toxic to the bacteria, it is known that the adverse effect can be minimized by secreting it to the outside of the cell. Usually, most of the proteins secreted through a cell membrane or inside membrane have a signal peptide at the N-terminal of the precursor thereof, and is cleaved by a signal peptidase in the secretion process to become a maturation protein. Most of the signal peptides have a basic amino acid, a hydrophobic amino acid, or a site of cleavage by a signal peptidase at the N-terminal thereof.

The objective protein can be secreted and expressed by placing a nucleic acid for coding for a known signal peptide typified by pelB (a signal peptide) at the 5' side of a nucleic acid for coding for the protein.

In the case where a biopolymer compound is formed as a composite of plural polypeptide chains, the polypeptide may be prepared respectively by separate vectors, but the plural polypeptide chains can be constructed by one vector. In this case, the secretion can be promoted by placing a nucleic acid for coding for pelb at the 5' side of the nucleic acid for coding for the domains or polypeptide chain. Further, for expression of a polypeptide chain having one or more domains, the secretion can be promoted by placing a nucleic acid for coding for pelB at the 5' terminal of the polypeptide chain in the same manner as above. The fused protein having a signal peptide at the N-terminal can be purified from a periplasma fraction and a culture supernatant.

For simplicity of the operation of purification of the expressed protein, a tag for purification can be provided genetically at the N-terminal or C-terminal of an antibody molecule, or a polypeptide chain formed by combining independent antibody fragments or plural antibody fragments. For example, the tag for purification is exemplified by a histidine tag composed of 6-residue sequence of histidine (hereinafter referred to as His×6), and a gluthathion-linking site of a glutathione-S-transferase (GST). The tag can be introduced by insertion of a nucleic acid for coding for the purification to 5'- or 3'-terminal of a nucleic acid for coding for gold-bonding protein in an expression vector into an intended position, by using a commercial vector for purification tag introduction, or by a like method.

An example of the process of the biopolymer by employing the aforementioned expression vector is described below.

The protein which is a biopolymer compound, or a polypeptide which is a constituting element of the protein is synthesized in a known host cell for protein expression by transforming the aforementioned protein-expressing vector designed for the host cell and using the protein synthesis system in the host cell. Then the intended protein is obtained by separating and purifying the cell liquid or a culture supernatant, For example, with Escherichia coli as the host cell, the protein can be allowed to secrete outside the cell by placing a nucleic acid for coding for a known signal peptide such as pelB at the 5' side of the nucleic acid.

Plural polypeptide chains having gold-bonding protein as a component element can be coded for in one expression vector. For this purpose, a nucleic acid for coding for pelB is placed at the 5' side of the nucleic acid for coding for the respective polypeptide chains as the constitution elements to promote the expressed protein outside the cell.

The gold-bonding protein having a signal peptide fused at the N-terminal can be purified from a periplasma fraction and a culture supernatant. For the purification, the protein component is concentrated from the fraction by ammonium sulfate or the like, suspended again in a suitable buffer solution, and purified: for example, by a nickel chelate column when a His tag is employed as the purification tag, and by a glutathione-immobilizing column when a GST is employed as the purification tag.

The gold-bonding protein expressed in a bacteria cell can be obtained as insoluble granules. The granules can be isolated by separating the bacterial mass from the liquid culture, crushing the bacterial mass by a French press or ultrasonic wave, and centrifuging the crushed cell liquid. The obtained insoluble granule fraction is solubilized by using a buffer solution containing a known modifying agent containing urea, or a guanidine hydrochloride salt, and purified by use of a purifying column under the modification conditions as above. The obtained column eluate fraction is subjected to a refolding treatment for removal of the modifier and reconstruction of the active structure. The refolding treatment may be conducted by any known method, including a stepwise dialysis, and dilution corresponding to the intended protein.

The domains and polypeptide chains of the gold-bonding protein can be expressed in the same host cell, or can be expressed in separate host cells and brought together to form a composite.

The vector containing the nucleic acid for coding for the gold-bonding protein is known to be capable of expressing the intended protein in vitro with a liquid cell extract. Suitable cells therefore include Escherichia coli, wheat germ, and rabbit retiform erythrocyte. However, since the protein synthesis from the cell-free liquid extract is conducted under reduction conditions, the conventional refolding treatment is preferred for formation of the disulfide linkage in the antibody fragment.

One of the bonding sites of the biopolymer compound for bonding to the porous body surface or to the capping member surface may be modified by introduction of a chemical modifying group into the biopolymer compound. For example, for a capping member having gold bared at least on a portion of the surface thereof, a biopolymer compound of the present invention can be prepared by introducing a group having an SH group at the terminal portion other than the bonding site for bonding to the porous body surface. On the other hand, to a biopolymer having a site for bonding to gold, a functional group having a silanol group or an alkoxysilane group may be introduced.

The bonding site of the connecting member for bonding to the porous body can be formed to have a peptide portion capable of bonding to the porous body. For a porous body having at least one of metals and metal oxides on at least a part of the surface, the connecting member can be constituted such that the bonding site of the connecting member connects with the portion containing at least one of the metals and metal oxides. Otherwise, for the porous body having silicon oxide on at least a part of the surface, the bonding site of the connecting member may be constituted so as to bond to the portion containing at least one of metals and metal oxides. The bonding site for bonding to the porous body can be a peptide having two or more of amino acid sequences selected form the group of amino acid sequences (1) SEQ ID NO:80, and amino acid sequences derived from (2) SEQ ID NO:81 by deletion, substitution, or addition of one or more amino acids.

(Releasable Substance)

The substance to be held by the structure of the present invention is selected to meet the use of the structure, being selected from various compounds and materials such as water-soluble drugs and fats soluble drugs.

(Controlled Release of Compound)

The retention and release of a substance in or from the structure of the present invention is controlled by an external stimulation, namely by loading of an external signal.

The external signal includes light, magnetism, and electricity. For DOS application, the signal is preferably harmless to a living body receiving the released compound. Therefore the light and the magnetism are preferred. The wavelength of the light is selected in consideration of influences on the capping member and the compound-receiving body. For example, a fine particle (particle size: 1-100 nm) having a core (particle size: 5-50 nm) coated with gold (coating thickness: 1-6 nm) generates heat by absorbing light of 800-1200 nm which is almost harmless to tissues and cells of animal bodies: The generated heat can break the bonding between the biopolymer compound and the capping member and disconnect the capping member from the porous body to release the compound to the outside of the structure.

A capping member which is formed from fine particulate gold is known to generate heat by application of a high frequency wave of 10 MHz to 2 GHz in a region from short wave to microwave. Such a change of a thermal property of the capping member can be utilized for disconnecting the capping member from the structure for the controlled compound release of the present invention. The light irradiation time is selected depending on the wavelength of the irradiated light.

The signal inputting apparatus for the release controlling means of the present invention is not limited provided that the apparatus is capable of changing the temperature of the periphery of the capping member connected to the porous body holding the substance of the present invention. For example, the apparatus may be a lamp for projecting a light beam of a wave length of 800 to 1200 nm, or may be a YAG laser, or the like, or may be any type of microwave-generating apparatus.

FIG. 1 illustrates schematically a process of release or diffusion of the drug. Drug 12 is held inside pore 11 of a porous body (13). Separately, a metal-coated fine silica particle 14 is prepared by coating a fine silica particle of 30 µm diameter with gold in a thickness of t=3 nm. Onto the surface of the fine silica particle, gold-bonding $F_V$ 15 fused with a silica-affinitive peptide is bonded. Thereby $F_V$ is bonded to the surface of the porous body constituting the opening of pore 11, and the fine particle 14 bonded with $F_V$ is held at the opening of the pore to close the pore (16). When the porous body is placed in a photomagnetic field, the fine particle absorbs energy (17) to generate heat. Consequently, the bonding of $F_V$ is broken and the fine particle is removed from the opening to release drug 12 from the pore outside by diffusion (18). Incidentally, drug 12 may be kept near the opening, not inside the pore provided that the drug is prevented from diffusion.

The structure of the present invention gives further second to seventh effects shown below.

As second effect, a porous body surface and a capping member surface can be specifically connected together through an organic compound as a connecting member including a biopolymer compound having capability of bonding to the porous body surface and to the capping member surface, especially an antibody, its fraction, or a peptide. Thereby, an adverse effect of bond formation between the connecting member and a substance not to be bonded thereto such as the releasable substance or a like interaction can be prevented. Therefore, higher specificity in recognition can be expected by use of a biopolymer compound which has a variable region of an antibody capable of bonding to the porous body surface and/or a variable region of an antibody capable of bonding to the capping member surface.

As a third effect, the porous body can be made stable in an environment of a body fluid such as blood by constituting the porous body at least partly from a metal or a metal oxide. Further, biocompatibility of the structure can be increased by forming the porous body from silicon oxide and the capping member from gold.

As a fourth effect, a releasable substance can be surely released from the porous body at an intended time and a site by designing the structure such that the capping member is disconnected by input of external stimulation (releasing signal) and the substance kept in the structure is released therefrom in accordance with the inputted signal.

As a fifth effect, the substance can be released by removal of the capping member by a slight temperature change that does not affect adversely the porous body constituting the structure, the substance kept in the porous body, and a treated portion of an objective patient, since a biopolymer compound is employed for physical or chemical connection of the porous body surface and the capping member surface.

As a sixth effect, the signal for inducing the release of the substance is inputted by at least one of light and a magnetic field change to cause temperature change at least on the surface of the capping member. The light and the magnetic field can be selected to be actually harmless, when applied, to treated animal bodies and human bodies. Therefore, an expensive equipment or apparatus is not necessary for the controlled release of the substance, and the application field will be widened.

As the seventh effect, the gold placed on at least a part of the capping member surface enables selection of the light or the magnetism change region to be harmless to the living body, and stable retention of the capping member surface to give long-term stability of the function of the controlled-release.

EXAMPLES

In Examples below, a structure is formed from mesoporous silica (SBA-15) as the porous body, gold-coated silica beads (gold layer: 1 nm, silica: 10 nm diameter) as the capping member, and a fused protein as biopolymer compound for connection prepared by fusion of an SBA-15-affinitive peptide to a C-terminal of a gold-bonding $_{SC}F_V$.

Example 1

Preparation of Porous Body

Mesoporous silica (SBA-15) is prepared by the procedure below.

A silica reaction solution is prepared from 4 g of a poly (ethylene oxide)-poly(propylene oxide)-poly(ethylene oxide) block copolymer constituted of 20 units of ethylene oxide, 70 units of propylene oxide, and 20 units of ethylene oxide (hereinafter referred to as $EO_{20}$-$PO_{70}$-$EO_{20}$); 0.041 mol of tetraethoxysilane (TEOS); 0.24 mol of HCl; and 6.67 mol of $H_2O$.

This silica reaction solution is allowed to react at 35° C. for 20 hours, and at 80° C. for 48 hours. The solution is further heated at 500° C. for 6 hours to burn the contained block copolymer resin $EO_{20}$-$PO_{70}$-$EO_{20}$ to obtain a porous silica.

The resulting porous silica has pores having an average pore diameter of 7.9 nm with an average silica wall thickness between the pores of 3 nm.

Example 2

Preparation of Fusion Protein of Gold-Bonding $_{sc}F_V$ and Peptide Affinitive to SBA-15

A protein formed by fusion of a peptide of SEQ ID NO:80 affinitive to SBA-15 to the C-terminal of a gold-$_{sc}F_V$ through the steps below.

(1) Preparation of Expression Vector

Figure 2B:
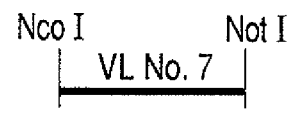
Figure 2C:
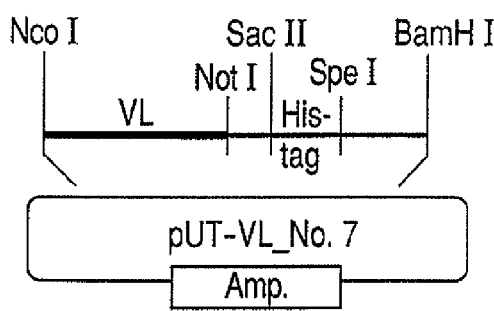
Figure 2D:
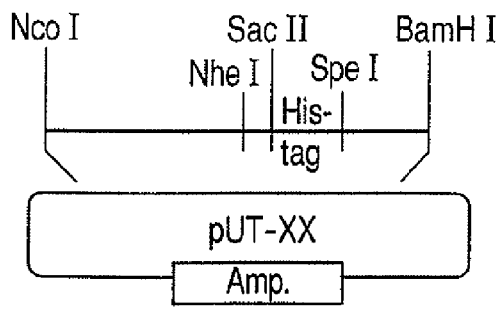
Figure 2E:
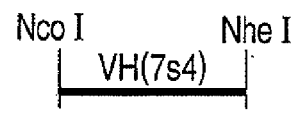
Figure 2F:
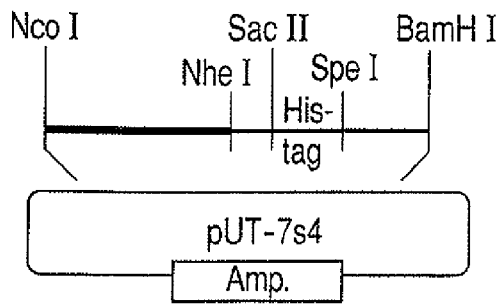
Figure 3A:
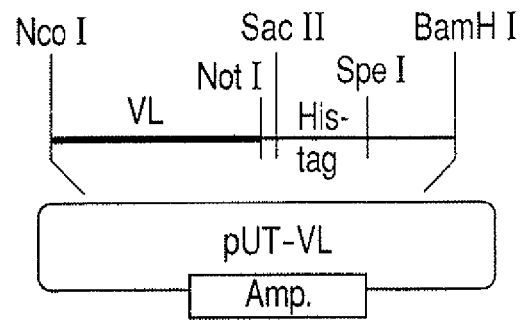
FIGS. 3A, 3B, and 3C illustrate examples of preparation of a vector for production of a biopolymer compound.
Figure 3B:
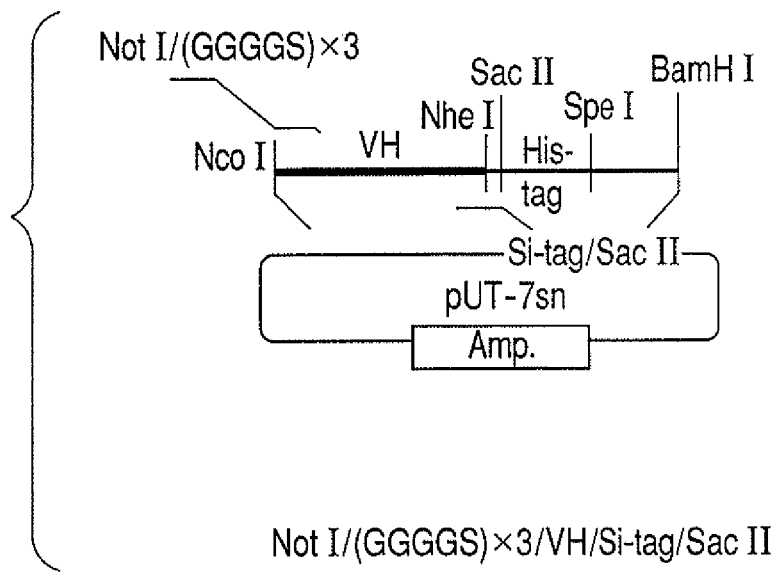
Figure 3C:
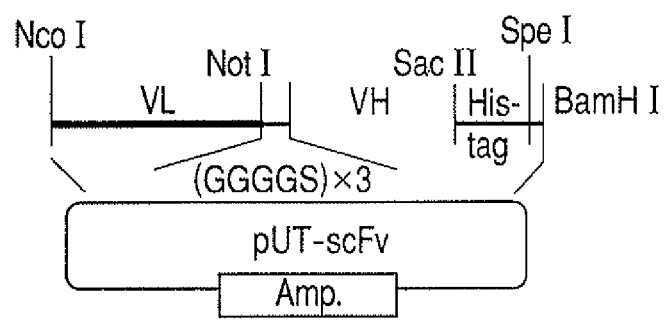

A plurality of sets of pET-15b (Novagen Co.) were modified by cutting the multiclonibng site thereof with NheI/SacII and NotI/SacII respectively to prepare two sets of pUT-XX as shown in FIGS. 2A and 2B. Next, VL (clone name: VL No. 7, SEQ ID No.76 and VH (clone name: 7s4, SEQ ID NO:60), which will become constituents of a gold-bolding $_{sc}F_V$, were inserted into the vectors pUT-XX, respectively. The resultant vectors are referred to as pUT-VL No. 7 and pUT-7s4, respectively. Then an expression vector pUT-$_{sc}F_V$ was prepared as below in which the VL-coding gene, a linker (SEQ ID NO:94×3), the VH-coding gene, a SBA-15-affinitive peptide (hereinafter may be referred to as "Si tag" as shown in FIGS. 3A to 3C) and a His×6 (hereinafter referred to as a His tag) are translated continuously and expresses it as a fusion protein (FIGS. 3A to 3C).

PCR is conducted with the above pUT-7s4 as a template and by using the primers below:
SiscF$_V$-B (SEQ ID NO:78)
SiscF$_V$-F (SEQ ID NO:79)

The PCR is conducted by using a commercial PCR kit (Takara Bio K.K., LA-Taq Kit) according to a protocol recommended by the supplier.

The obtained PCR product is subjected to 2%-agarose electrophoresis, and roughly purified by a gel of a gel extraction kit (Promega Co.) to obtain a PCR fraction of about 400 bp. The product is confirmed to have the intended base sequence by sequencing. pUT-VL No. 7 and the PCR fragment obtained in the above PCR are cut by NotI/SacII. The products are subjected to agarose electrophoresis, and the intended fragments are purified at the vector side and the insert side.

The obtained purified nucleic acid fragment is mixed at a ratio of Vector:Insert=1:5 and the mixture is subjected to a ligation reaction in the same manner as in Example 1.

With the above ligation reaction liquid, JM109 competent cell 40 μL is transformed. The transformation is conducted by heat shock by temperature change from an ice temperature to 42° C. for 90 sec to an ice temperature. To the above BL21 solution after transformation by heat shock, 750 μL of an LB culture is added and the mixture is cultivated at 37° C. for one hour by shaking. Then the culture is centrifuged at 6000 rpm for 5 minutes. A 650 μL portion of the supernatant liquid of the culture is discarded. The remaining supernatant liquid and the precipitated cell fraction are stirred, spread on an LB/amp. plate, and left standing at 37° C. overnight.

From the plate, colonies are picked out at random, and are cultivated in 3 mL of an LB/amp. liquid culture by shaking. Therefrom, a plasmid is extracted by a commercial MiniPrep kit (Promega Co.) according to a method recommended by the supplier. The obtained plasmid is cut by NotI/SacII. The product is subjected to agarose electrophoresis to confirm the insertion of the intended gene fraction. This plasmid is referred to a pUT-$_{sc}F_V$Sp.

With the plasmid pUT-$_{sc}F_V$Sp obtained in the above operation, BL21 (DE3) competent cell 40 μL is transformed. The transformation is conducted by heat shock by temperature change from an ice temperature to 42° C. for 90 sec and to an ice temperature.

To the above BL21 solution after transformation by heat shock, 750 μL of an LB culture is added and the mixture is cultivated at 37° C. for one hour by shaking. Then the culture is centrifuged at 6000 rpm for 5 minutes. A 650 μL portion of the supernatant liquid of the culture is discarded. The remaining supernatant liquid and the precipitated cell fraction are stirred, spread on an LB/amp. plate, and left standing at 37° C. overnight.

(2) Preliminary Cultivation

From the plate, colonies are picked out at random, and are cultivated in 3.0 mL of an LB/amp. liquid culture at 28° C. overnight by shaking.

(3) Main Cultivation

The above preliminary cultivation liquid is inoculated to 750 mL of a 2×YT culture, and cultivation is continued at 28° C. At the time when the OD600 exceeds a level of 0.8, IPTG is added thereto to a final concentration of 1 mM. The mixture is further cultivated at 28° C. overnight.

(4) Purification

Through Steps (A) to (E) below, the intended polypeptide chain is recovered from the insoluble granule fraction, and is purified.

(A) Recovery of Insoluble Granules

The culture liquid obtained in the above Step (3) is centrifuged at 6000 rpm for 30 minutes to obtain a bacterial mass fraction as a precipitate. The bacterial mass is suspended in 15 mL of a tris solution (20 mM tris/500 mM NaCl) on an ice bath. The liquid suspension is crushed by a French press to obtain a crushed cell liquid. The crushed cell liquid is centrifuged at 12000 rpm for 15 minutes. The supernatant liquid is removed to obtain an insoluble granule fraction as a precipitate.

(B) Solubilization of Insoluble Granule Fraction

The insoluble fraction obtained in Step (A) is immersed in 10 mL of 6M guanidine hydrochloride/tris solution overnight. The solution is centrifuged at 12000 rpm for 10 minutes to obtain a solubilized solution as the supernatant liquid.

(C) Metal Chelate Column

His-Bind (Novagen Co.) is used as a stationary phase of a metal chelate column. The column preparation, sample loading, and washing are conducted according to the method recommended by the supplier at room temperature (20° C.). The intended His-tagged fusion polypeptide is eluted by a 60 mM imidazole/tris solution. The SDS-PAGE (acrylamide 15%) measurement of the eluate shows a single band, whereby the polypeptide is confirmed to be purified.

(D) Dialysis

The above eluate is dialyzed by use of a 6M guanidine hydrochloride/tris solution as the external liquid at 4° C. to remove the imidazole from the eluate and to obtain the respective polypeptide chain solution.

(E) Refolding

In the same manner as above, the solutions of the polypeptide chains of $_{sc}F_v$-Sp, a fusion product of the gold-bonding $F_v$ and the above peptide, are respectively refolded with simultaneous removal of guanidine hydrochloride by dialysis at 4° C. through Steps (a) to (g) below.

(a) Polypeptide chain samples are prepared with a 6M guanidine hydrochloride/tris solution at a concentration of 7.5 µM (volume 10 mL after dilution) by measuring the molar extinction coefficient and the value ΔO.D. (280-320 nm) of the respective polypeptide chains. To the sample solutions, β-mercaptoethanol (reducing agent) is added to a final concentration of 375 µM (50 times the protein concentration) and reducing reaction is allowed to proceed at room temperature in the dark for 4 hours. This sample solutions are put into a dialysis bag (MWCO: 14,000) for dialysis.

(b) The samples for dialysis are immersed in a 6M guanidine hydrochloride/tris solution as the external solution for dialysis. Dialysis is conducted with gentle stirring for 6 hours, (c) The concentration of the external solution is lowered stepwise to 3M, and 2M. The dialysis is conducted at each of the external solution concentrations for six hours.

(d) To a tris solution, are added an oxidation type glutathione (GS-SG) to a final concentration of 375 µM, and L-Arg to a final concentration of 0.4 M. This tris solution is added to the 2M dialysis external solution of the above Step (c) to bring the guanidine hydrochloride concentration to 1 M, and the pH of the mixture solution is adjusted to pH 8.0 (4° C.) by NeOH. With this solution, the dialysis is continued with gentle stirring for 12 hours.

(e) In the same manner as in the above Step (d), an L-Arg-containing tris solution containing 0.5 M guanidine hydrochloride is prepared, and the dialysis is continued with this solution for further 12 hours.

(f) Finally the dialysis is conducted in the tris solution for 12 hours.

(g) After the dialysis, the agglomerate and the supernatant are separated by centrifugation at 10000 rpm for about 20 minutes. The solution obtained above is subjected to SPR measurement by replacing the external solution to a phosphate buffer (hereinafter referred to as PBS). Thereby the property of bonding to gold is confirmed.

Example 3

Preparation of Structure (1) A 200 mg portion of SBA-15 prepared in Example 1 is immersed in a 3 µM ATP/phosphate buffer solution; PBS (pH 7.4) overnight.

(2) A fine particulate gold (20 nm, produced by Tanaka Kikinzoku K.K., 0.15 mmol) is suspended in 0.01 mmol ATP/PBS.

(3) The 1.5 µM $_{sc}F_v$/PBS fused with silica-affinitive peptide prepared in Example 2 is mixed with the immersion-treated SBA-15 of Step (1) and the suspension of Step (2), and the mixture is stirred for 24 hours.

(4) Then the suspension is centrifuged at 12000 rpm for 5 minutes to remove the supernatant to obtain a precipitate. This precipitate is vacuum-dried to obtain a structure.

Example 4

Controlled Release of Compound from Structure-1

(1) A 20 mg portion of the structure obtained in Example 3 is suspended in a PBS (pH 7.4) and is dispersed in the solution by application of an ultrasonic wave. This operation is repeated three times to wash off the adsorbed ATP.

(2) The above structure is kept standing in a state of suspension for 12 hours. At 0, 4, 8, and 12 hours of the standing, a portion of the solution is taken out. The respective portions are subjected to measurement by HPLC (C18, reversed phase column, detection wavelength: 275 nm). The amount of ATP is confirmed to decrease with time.

(3) Then a YAG laser light (1064 nm, 164 mJ/pulser 7 nsec, 10 Hz) is projected thereto for one hour.

(4) During the laser irradiation, a sample is taken out from the solution in every 10 minutes and is subjected to HPLC analysis. Thereby ATP is confirmed to be released with time.

Example 5

Controlled Release of Compound from Structure-2

(1) A 20 mg portion of the structure obtained in Example 3 is suspended in a PBS (pH 7.4) and is dispersed in the solution by application of an ultrasonic wave. This operation is repeated three times to wash off the adsorbed ATP.

(2) The above structure is kept standing in a state of suspension for 12 hours. At 0, 4, 8, and 12 hours of the standing, a portion of the solution is taken out. The respective portions are subjected to measurement by HPLC (C18, reversed phase column, detection wavelength: 275 nm). The amount of ATP is confirmed to decrease with time.

(3) Then a light beam of 0.5 GHz is projected thereto intermittently five times at a cycle of 10 seconds of projection and 50 seconds of interruption by a synthesized signal-generation apparatus (HP Co.).

(4) After the signal projection, a sample is taken out from the solution and is subjected to HPLC analysis. The amount of the ATP increases in comparison with an amount of ATP in the solution in Step (2). This shows that the ATP is released by the light signal.

Example 6

A protein is prepared, using a VH (VH clone name: A14P-7s4, SEQ ID NO: 83) corresponding to a base sequence represented by SEQ ID NO:82, which VH was introduced by replacing the fourteen amino acid residue, alanine, of VH in the gold-bonding scF$_v$-SBA-15-affinitive peptide employed in Example 2 with proline.

Preparation of Expression Plasmid:

A variation is introduced to the intended position by using, as a template, pUT-$_{sc}F_v$Sp obtained in Example 2. The variation is introduced by means of QuickChange Kit (Stratagen Co.) according to a method recommended by the supplier. The primers below are employed.

A14P-f [SEQ ID NO:84]

A14P-r [SEQ ID NO:85]

By sequencing, the obtained plasmid is confirmed to have the intended DNA coding the amino acid sequence represented by the SEQ ID NO:80.

By use of the plasmid pUT-$_{sc}$F$_v$2Sp, BL21 (DE3) competent cell 40 µL is transformed by heat shock by temperature change from an ice temperature to 42° C. for 90 seconds and to an ice temperature.

To the above BL21 solution having been transformed by the heat shock, 750 µL of an LB culture is added. The mixture is cultivated at 37° C. for one hour by shaking.

The culture is centrifuged at 6000 rpm for 5 minutes. A 650 µL portion of the culture supernatant is discarded, and the remaining supernatant and the precipitated cell fraction are stirred. This mixture is spread on an LB/amp. plate, and is kept standing at 37° C. overnight.

Then, the intended protein is obtained in the same manner as in Steps (2) to (4) in Example 2. A structure is prepared by use of the obtained protein in the same manner as in Example 3.

The evaluation is made in/the same manner as in example 3 and it is confirmed that the ATP is released in the same manner as in Example 4.

Example 7

A protein is prepared which corresponds to VH (VH clone name: PFER-7s4, SEQ ID NO:87) represented by SEQ ID NO:86. The protein has constitution of the VH (VH clone name: A14P) of the gold-bonding $_{sc}$F$_v$-SBA-15-affinitive peptide employed in Example 6 in which the valine at 34$^{th}$ position is changed to phenylalanine and the glutamine at 44$^{th}$ position is changed to glutamic acid, and the leucine at 45$^{th}$ position is changed to arginine.

Preparation of Expression Plasmid:

Variations are introduced to the intended positions by using, as a template, pUT-$_{sc}$F$_v$2Sp obtained in Example 6. The variations are introduced by means of QuickChange Kit (Stratagen Co.) according to a method recommended by the supplier. The intended plasmid is obtained by three operations. The primers below are employed.

PCR primer for the first variation introduction
   V37F-f [SEQ ID NO:88]
   V37F-r [SEQ ID NO:89]

PCR primer for the second variation introduction
   G44E-f [SEQ ID NO:90]
   G44E-r [SEQ ID NO:91]

PCR primer for the third variation introduction
   L45F-f [SEQ ID NO:92]
   L45F-r [SEQ ID NO:93]

By sequencing, the obtained plasmid is confirmed to have the intended DNA represented by the SEQ ID NO:82 inserted therein.

By use of the plasmid pUT-$_{sc}$F$_v$2Sp obtained by the above operation, BL21 (DE3) competent cell 40 µL is transformed by heat shock by temperature change from an ice temperature to 42° C. for 90 seconds and to an ice temperature.

To the above BL21 solution having been transformed by the heat shock, 750 µL of an LB culture is added. The mixture is cultivated at 37° C. for one hour by shaking.

The culture is centrifuged at 6000 rpm for 5 minutes. A 650 µL portion of the culture supernatant is discarded, and the remaining supernatant and the precipitated cell fraction are stirred. This mixture is spread on an LB/amp. plate, and is kept standing at 37° C. overnight.

Then, the intended protein is obtained in the same manner as in Steps (2) to (4) in Example 2. A structure is prepared by use of the obtained protein in the same manner as in Example 3.

The evaluation is made in the same manner as in example 3 and it is confirmed that the ATP is released in the same manner as in Example 4.

INDUSTRIAL APPLICABILITY

The present invention provides a structure comprising at least a porous body holding one or more compounds, and comprising (1) a capping member for keeping the compound in a pore or a periphery thereof, and (2) a material for connecting the capping member and the surface of the porous body physically or chemically, the material comprising an organic compound having a biopolymer as at least a part thereof. According to the present invention, a structure can be provided which is capable of holding a compound stably in the porous body. The present invention provides also a means for controlling the release of the compound from the structure. According to the present invention, the compound held by the structure can be released at a desired timing from the structure.

The present invention enables supply of an intended substance suitably in a chemical reaction. By application of the present invention to drug delivery systems, the intended substance can be released by applying a signal from the outside to a diseased portion only, whereby the amount of a drug dosed to a patient can be minimized to decrease adverse effects such as a side effect.

What is claimed is:

1. A structure for holding a compound inside of the structure, comprising:
   a porous body having pores with a diameter ranging from 1 nm to 10 μm which comprises silicon oxide;
   a capping member for covering at least a part of an opening of at least one of the pores; and
   a connecting member for connecting the capping member to a surface of the porous body,
   wherein, the capping member is a particle at least the surface of which particle comprises gold, and the diameter of the capping member is greater than the size of the opening of the pores of the porous body, and
   wherein the connecting member comprises at least one variable region of an antibody which region comprises the amino acid sequence of SEQ ID NO: 60 and binds to the gold.

* * * * *